US007883846B2

(12) United States Patent
Miesenbock et al.

(10) Patent No.: US 7,883,846 B2
(45) Date of Patent: Feb. 8, 2011

(54) HETEROLOGOUS STIMULUS-GATED ION CHANNELS AND METHODS OF USING SAME

(75) Inventors: Gero Miesenbock, New York, NY (US); Boris Zemelman, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1131 days.

(21) Appl. No.: 10/452,879

(22) Filed: Jun. 2, 2003

(65) Prior Publication Data

US 2004/0023203 A1    Feb. 5, 2004

Related U.S. Application Data

(60) Provisional application No. 60/384,670, filed on May 31, 2002, provisional application No. 60/441,452, filed on Jan. 21, 2003.

(51) Int. Cl.
  *C12Q 1/68* (2006.01)
(52) U.S. Cl. .......................................................... 435/6
(58) Field of Classification Search ..................... 435/6, 435/69.1, 320.1
  See application file for complete search history.

(56) References Cited

U.S. PATENT DOCUMENTS 6,335,180 B1    1/2002   Julius et al. ................ 435/69.1
2004/0236377 A1*  11/2004  Stokes et al. .................... 607/3

FOREIGN PATENT DOCUMENTS

WO         WO01/83752 A2    11/2001

OTHER PUBLICATIONS

Guyton, 1986, Textbook of Medical Physiology, Seventh Edition W.B. Saunders Company, p. 395.; pp. 582-583.*
Webster's Seventh New Collegiate Dictionary p. 780.*
Savidge et al., Comparison of intracellular calcium signals evoked by heat and capsaicin in cultured rat dorsal root ganglion neurons and in a cell line expressing the rat vanilloid receptor, VR1 Neuroscience vol. 102, Issue 1, Jan. 2, 2001, pp. 177-184.*
Guo et al., Protein tolerance to random amino acid change.Proc Natl Acad Sci U S A. Jun. 22, 2004;101(25):9205-10. Epub Jun. 14, 2004.*
Voet, Biochemistry John Wiley and Sons, 1990, pp. 126-128.*
Kimchi-Sarfaty C et al., A "silent" polymorphism in the MDR1 gene changes substrate specificity.Science. Jan. 26, 2007;315(5811):525-8.*
Awatramani, An Flp indicator mouse expressing alkaline phosphatase from the ROSA26 locus, Nature Genetics, 2001, pp. 257-259, vol. 29.
Bainbridge et al., In vivo gene transfer to the mouse eye using an HIV-based lentiviral vector: efficient long-term transduction of corneal endothelium and retinal pigment epithelium, Gene Therapy, 2001, pp. 1665-1668, vol. 8.

Bex et al., Controlling Gene Expression in the Urothelium using Transgenic Mice with Inducible Bladder Specific Cre-Lox Recombination, The Journal of Urology, 2002, pp. 2641-2644, vol. 168.
Birder et al., Altered urinary bladder function in mice lacking the vanilloid receptor TRPV1, Nature Neuroscience, 2002, pp. 856-860, vol. 5, No. 9.
Bishop et al., Unnatural Ligands for Engineered Proteins: New Tools for Chemical Genetics, Annu. Rev. Biophys. Biomol. Struct., 2000, pp. 577-606, vol. 29.
Brake et al., New structural motif for ligand-gated ion channels defined by an ionotropic ATP receptor, Nature, 1994, pp. 519-523, vol. 371.
Brake et al., Signaling by Extracellular Nucleotides, Annu. Rev. Cell Dev. Biol., 1996, pp. 519-541, vol. 12.
Campfield et al., Strategies and Potential Molecular Targets for Obesity Treatment, Science, 1998, pp. 1383-1387, vol. 280.
Cao et al., Profiling brain transcription: neurons learn a lesson from yeast, Current Opinion in Neurobiology, 2001, pp. 615-620, vol. 11, No. 5.
Carbon et al., Modulation of regional brain function by deep brain stimulation: studies with positron emission tomography, Current Opinion Neurol., 2002, pp. 451-455, vol. 15, No. 4.
Caterina et al., The capsaicin receptor: a heat-activated ion channel in the pain pathway, Nature, 1997, pp. 816-824, vol. 389.
Caterina et al., The Vanilloid Receptor: A Molecular Gateway to the Pain Pathway, Annu. Rev. Neurosci., 2001, pp. 487-517, vol. 24.
Clapham et al., The TRP Ion Channel Family, Nature Reviews / Neuroscience, 2001, pp. 387-396, vol. 2.
Crawley et al., A Proposed Test Battery and Constellations of Specific Behavioral Paradigms to Investigate the Behavioral Phenotypes of Transgenic and Knockout Mice , Hormones and Behavior, 1997, pp. 197-211, vol. 31, No. 3.
Crawley, Behavioral phenotyping of transgenic and knockout mice: experimental design and evaluation of general health, sensory functions, motor abilities, and specific behavioral tests, Brain Research, 1999, pp. 18-26, vol. 835, No. 1.
Ding et al., Inactivation of $P2X_2$ purinoceptors by divalent cations, Journal of Physiology, 2000, pp. 199-214, vol. 522, Pt 2.

(Continued)

*Primary Examiner*—Maria Leavitt
(74) *Attorney, Agent, or Firm*—Larson & Anderson, LLC

(57) ABSTRACT

Methods and compositions to activate a genetically designated target cell (or population of target cells) artificially, in vivo or in vitro, employ triggering of heterologous stimulus-gated ion channels to activate the cells. The stimulus-gated ion channels are suitably TRPV1, TRPM8 or $P2X_2$. A stimulus which leads to opening or "gating" of the ion channel can be a physical stimulus or a chemical stimulus. Physical stimuli can be provided by heat, or mechanical force, while chemical stimuli can suitably be a ligand, such as capsaicin for TRPV1 or ATP for $P2X_2$, or a "caged ligand," for example a photolabile ligand derivative, in which case a physical signal in the form of light is used to provide the chemical signal. Selective activation of the cell may be used for various applications including neuronal and neuroendocrine mapping and drug screening.

50 Claims, 9 Drawing Sheets

OTHER PUBLICATIONS

Follenzi, Efficient Gene Delivery and Targeted Expression to Hepatocytes In Vivo by Improved Lentiviral Vectors, Human Gene Therapy, 2002, pp. 243-260, vol. 13, No. 2.

Frohman et al., Rapid production of full-length cDNAs from rare transcripts: Amplification using a single gene-specific oligonucleotide primer, Proc. Natl. Acad. Sci. USA, 1988, pp. 8998-9002, vol. 85, No. 23.

Georgopoulos et al., Generation and Characterization of Two Transgenic Mouse Lines Expressing Human ApoE2 in Neurons and Glial Cells, Biochemistry, 2002, pp. 9293-9301, vol. 41, No. 30.

Gossen et al., Studying Gene Function in Eukaryotes by Conditional Gene Inactivation, Annu. Rev. Genet., 2002, pp. 153-173, vol. 36.

Gusella et al., Lentiviral Gene Transduction of Kidney, Human Gene Therapy, 2002, pp. 407-414, vol. 13, No. 3.

Hoess et al., Interaction of the bacteriophage P1 recombinase Cre with the recombining site loxP, Proc. Natl. Acad. Sci. USA, 1984, pp. 1026-1029, vol. 81, No. 4.

Hoess et al., Mechanism of Strand Cleavage and Exchange in the Cre-lox Site-specific Recombination System, J. Mol. Biol., 1985, pp. 351-362, vol. 181, No. 3.

Hofmann et al., Overexpression of Low Density Lipoprotein (LDL) Receptor Eliminates LDL from Plasma in Transgenic Mice, Science, 1988, pp. 1277-1281, vol. 239, No. 4845.

Houdebine,The methods to generate transgenic animals and to control transgene expression, Journal of Biotechnology, 2002, pp. 145-160, vol. 98, No. 2-3.

Jackson et al., The novel mechanism of initiation of picornavirus RNA translation, Trends in Biochem Science, 1990, pp. 477-483, vol. 15, No. 12.

Jang et al., A Segment of the 5' Nontranslated Region of Encephalomyocarditis Virus RNA Directs Internal Entry of Ribosomes during in vitro translation, Journal of Virology, 1988, pp. 2636-2643, vol. 62, No. 8.

Jerecic et al., Impaired NMDA receptor function in mouse olfactory bulb neurons by tetracycline-sensitive NR1 (N598R) expression, Molecular Brain Research, 2001, pp. 96-104, vol. 94, No. 1-2.

Kaplan et al., Rapid Photolytic Release of Adenosine 5'-Triphosphate from a Protected Analogue: Utilization by the Na:K Pump of Human Red Blood Cell Ghosts, Biochemistry, 1978, pp. 1929-1935, vol. 17, No. 10.

Kobinger et al., Filovirus-pseudotyped lentiviral vector can efficiently and stably transduce airway epithelia in vivo, Nature Biotechnology, 2001, pp. 225-230, vol. 19, No. 3.

Kozloski et al., Stereotyped Position of Local Synaptic Targets in Neocortex, Science, 2001, pp. 868-872, vol. 293, No. 5531.

Kugler et al., Neuron-Specific Expression of Therapeutic Proteins: Evaluatin of Different Cellular Promoters in Recombinant Adenoviral Vectors, Molecular Cell Neuroscience, 2001, pp. 78-96, vol. 17, No. 1.

Kuner et al., A Genetically Encoded Ratiometric Neurotechnique Indicator for Chloride: Capturing Chloride Transients in Cultured Hippocampal Neurons, Neuron, 2000, pp. 447-459, vol. 27, No. 3.

Lavon et al., High susceptibility to bacterial infection, but no liver dysfunction, in mice compromised for hepatocyte NF-kB activation, Nature Medicine, 2000, pp. 573-577, vol. 6, No. 5.

Lewandoski, Conditional Control of Gene Expression in the Mouse, Nature Reviews, 2001, pp. 743-755, vol. 2, No. 10.

Liu et al., Versatile Regulation of Cytosolic $Ca^{2+}$ by Vanilloid Receptor I in Rat Dorsal Root Ganglion Neurons, The Journal of Biological Chemistry, 2003, pp. 5462-5472, vol. 278, No. 7.

Lois et al., Germline Transmission and Tissue-Specific Expression of Transgenes Delivered by Lentiviral Vectors, Science, 2002, pp. 868-872, vol. 295, No. 5556.

Marriott, Caged Protein Conjugates and Light-Directed Generation of Protein Activity: Preparation, Photoactivation, and Spectroscopic Characterization of Caged G-actin Conjugates, Biochemistry, 1994, pp. 9092-9097, vol. 33, No. 31.

Mccray, Properties and Uses of Photoreactive Caged Compounds, Annu. Rev. Biophys. Chem., 1989, pp. 239-270, vol. 18.

Mckemy et al., Identification of a cold receptor reveals a general role for TRP channels in thermosensation, Nature, 2002, pp. 52-58, vol. 416, No. 6876.

Miesenbock et al., Visualizing secretion and synaptic transmission with pH-sensitive green fluorescent proteins, Nature, 1998, pp. 192-195, vol. 394, No. 6689.

Miyawaki et al., Fluorescent indicators for ca2+ based on green fluorescent proteins and calmodulin, Nature, 1997, pp. 882-887, vol. 388, No. 6645.

Miyazaki et al., Expression vector system based on the chicken β-actin promoter directs efficient production of interleukin-5, Gene, 1989, pp. 269-277, vol. 79, No. 2.

Mochizuki et al., High-Titer Human Immunodeficiency Virus Type 1-Based Vector Systems for Gene Delivery into Nondividing Cells, Journal of Virology, 1998, pp. 8873-8883, vol. 72, No. 11.

Montell et al., The TRP Channels, a Remarkably Functional Family, Cell, 2002, pp. 595-598, vol. 108, No. 5.

Moriyoshi et al., Labeling Neural Cells Using Adenoviral Gene Transfer of Membrane-Targeted GFP, Neuron, 1996, pp. 255-260, vol. 16, No. 2.

Nakai et al., A high signal-to-noise Ca2+ probe composed of a single green fluorescent protein, Nature Biotechnology, 2001, pp. 137-141, vol. 19, No. 2.

Naldini et al., In Vivo Gene Delivery and Stable Transduction of Nondividing Cells by a Lentiviral Vector, Science, 1996, pp. 263-267, vol. 272, No. 5259.

Nery et al., The caudal ganglionic eminence is a source of distinct cortical and subcortical cell populations, Nature Neuroscience, 2002, pp. 1279-1287, vol. 5, No. 12.

Nicolelis et al., Multielectrode recordings: the next steps, Current Opinion Neurobiology, 2002, pp. 602-606, vol. 12, No. 5.

Ozturk-Winder et al., The murine whey acidic protein promoter directs expression to human mammary tumors after retroviral transduction, Cancer Gene Therapy, 2002, pp. 421-431, vol. 9, No. 5.

Peier et al., A TRP Channel that Senses Cold Stimuli and Menthol, Cell, 2002, pp. 705-715, vol. 108, No. 5.

Rapp, Flash Lamp-Based Irradiation of Caged Compounds, Methods in Enzymology, 1998, pp. 202-222, vol. 291.

Rockenstein et al., Differential Neuropathological Alterations in Transgenic Mice Expressing α-synuclein From the Platelet-derived Growth Factor and Thy-1 Promoters, Journal of Neuroscience Research, 2002, pp. 568-578, vol. 68, No. 5.

Sankaranarayanan et al., Calcium accelerates endocytosis of vSNAREs at hippocampal synapses, Nature Neuroscience, 2001, pp. 129-136, vol. 4, No. 2.

Schwartz et al., Central nervous system control of food intake, Nature, 2000, pp. 661-671, vol. 404, No. 6778.

Shimozono et al., Confocal Imaging of Subcellular Ca2+ Concentrations Using a Dual-Excitation Ratiometric Indicator Based on Green Fluorescent Protein, Science STKE, 2002, No. 125: PL4.

Soriano, Generalized lacZ expression with the ROSA26 Cre reporter strain, Nature Genetics, 1999, pp. 70-71, vol. 21, No. 1.

Srinivas et al., Cre reporter strains produced by targeted insertion of EYFP and ECFP into the ROSA26 locus, BMC Dev Biol, 2001, vol. 1, No. 1:4.

Stanford et al., Gene-Trap Mutagenesis: Past, Present and Beyond, Nature Review Genetics, 2001, pp. 756-768, vol. 2, No. 10.

St. John et al., Analysis and Isolation of Embryonic Mammalian Neurons by Fluorescence-Activated Cell Sorting, The Journal of Neuroscience, 1986, pp. 1492-1512, vol. 6, No. 5.

Tobin et al., Combinatorial Expression of TRPV Channel Proteins Defines Their Sensory Functions and Subcellular Localization in *C. elegans* Neurons, Neuron, 2002, pp. 307-318, vol. 35, No. 2.

Tomomura et al., Purification of Purkinje cells by fluorescence-activated cell sorting from transgenic mice that express green fluorescent protein, European Journal of Neuroscience, 2001, pp. 57-63, vol. 14, No. 1.

Townley et al., Rapid Sequence Analysis of Gene Trap Integrations to Generate a Resource of Insertional Mutations in Mice, Genome Research, 1997, pp. 293-298, vol. 7, No. 3.

Valera et al., A new class of ligand-gated ion channel defined by $P_{2x}$ receptor for extracellular ATP, Nature, 1994, pp. 516-519, vol. 371, No. 6497.

Walker et al., Photolabile Protecting Groups for an Acetylcholine Receptor Ligand, Synthesis and Photochemistry of a New Class of o-nitrobenzyl derivatives and their effects on receptor function, Biochemistry, 1986, pp. 1799-1805, vol. 25, No. 7.

Walker et al., Synthesis and Properties of Caged Nucleotides, Methods in Enzymology, 1989, p. 288-301, vol. 172, 288-301.

Walpole et al., Analogues of Capsaicin with Agonist Activity as Novel Analgesic Agents; Structure—Activity Studies. 1. The Aromatic A-Region, J. Med. Chem., 1993, pp. 2362-2372, vol. 36, No. 16.

Walpole et al. Similarities and Differences in the Structure—Activity Relationships of Capsaicin and Resiniferatoxin Analogues, J. Med. Chem., 1996, pp. 2939-2952, vol. 39, No. 15.

Watson et al., Targeted Transduction Patterns in the Mouse Brain by Lentivirus Vectors Pseudotyped with VSV, Ebola, Mokola, LCMV, or MuLV Envelope Proteins, Molecular Therapy, 2002, pp. 528-537, vol. 5, No. 5 Pt 1.

Wilcox et al., Synthesis of Photolabile "Precursors" of Amino Acid Neurotransmitters, J. Org. Chem., 1990, pp. 1585-1589, vol. 55.

Wool-Lewis et al., Characterization of Ebola Virus Entry by Using Pseudotyped Viruses: Identification of Receptor-Deficient Cell Lines, Journal of Virology, 1998, pp. 3155-3160, vol. 72, No. 4.

Yamaoka et al., Transgenic Expression of FGF8 and FGF10 Induces Transdifferentiation of Pancreatic Islet Cells into Hepatocytes and Exocrine Cells, Biochemical and Biophysical Research Communications, 2002, pp. 138-143, vol. 292, No. 1.

Zemelman et al., Genetic schemes and schemata in neurophysiology, Current Opinion Neurobiology, 2001, pp. 409-414, vol. 11.

Zemelman et al., Selective Photostimulation of Genetically ChARGed Neurons, Neuron, 2002, pp. 15-22, vol. 33, No. 1.

Zinyk et al., Fate mapping of the mouse midbrain-hindbrain constriction using a site-specific recombinatin system, Current Biology, 1998, pp. 665-668, vol. 8, No. 11.

Zufferey et al., Multiply attenuated lentiviral vector achieves efficient gene delivery in vivo, Nature Biotechnology, 1997, pp. 871-875, vol. 15, No. 9.

Arnold et al., A calcium responsive element that regulates expression of two calcium binding proteins in Purkinje cells, Proc. Natl. Acad. Sci. USA, 2003, pp. 8842-8847, vol. 94, No. 16.

Beyer et al., Oncoretrovirus and Lentivirus Vectors Pseudotyped with Lymphocytic Choriomeningitis Virus Glycoprotein: Generation, concentration, and broad host range, Journal of Virology, 2002, pp. 1488-1495, vol. 76, No. 3.

Callaway et al., Photostimulation using caged glutamate reveals functional circuitry in living brain slices, Proc. Natl. Acad. Sci. USA, 1993, pp. 7661-7665, vol. 90.

Defalco et al., Virus-Assisted mapping of Neural Inputs to a Feeding Center in the Hypothalamus, Science, 2001, pp. 2608-2613, vol. 291.

Eberwine et al., mRNA Expression Analysis of Tissue Sections and Single Cells, The Journal of Neuroscience, 2001, pp. 8310-8314, vol. 21, No. 21.

Friedman et al., Leptin and the regulation of body weight in mammals, Nature, 1998, pp. 763-770, vol. 395.

Guler et al., Heat-Evoked Activation of the Ion Channel, TRPV4, The Journal of Neuroscience, 2002, pp. 6408-6414, vol. 22, No. 15.

Herrera, Adult insulin- and glucagon-producing cells differentiate from two independent cell lineages, Development, 2000, pp. 2317-2322, vol. 127.

Jiang et al., Fate of the mammalian cardiac neural crest, Development, 2000, pp. 1607-1616, vol. 127, No. 8.

Jiang et al., Retinoblastoma Gene Promoter Directs Transgene Expression Exclusively to the Nervous System, 2001, pp. 593-600, vol. 276, No. 1.

Kang et al., In Vivo Gene Transfer Using a Nonprimate Lentiviral Vector Pseudotyped with Ross River Virus Glycoproteins, Journal of Virology, 2002, pp. 9378-9388, vol. 76, No. 18.

Lee et al., Conditional lineage ablation to model human diseases, Proc. Natl. Acad. Sci. USA, 1998, pp. 11371-11376, vol. 95, No. 19.

Leighton et al., Defining brain wiring patterns and mechanisms through gene trapping in mice, Nature, 2001, pp. 174-179, vol. 410.

Makinae et al., Structure of the Mouse Glutamate Decarboxylase 65 Gene and Its Promoter. Preferential Expression of Its Promoter in the GABAergic Neurons of Transgenic Mice, Journal of Neurochemistry, 2000, pp. 1429-1437, vol. 75, No. 4.

Marshall et al., Activation of vanilloid receptor 1 by resiniferatoxin mobilizes calcium from inositol 1,4,5-trisphosphate-sensitive stores, British Journal of Pharmacology, 2003, pp. 172-176, vol. 138, No. 1.

Matsui et al., Phenotypic Spectrum Caused by Transgenic Overexpression of Activated Akt in the Heart, The Journal of Biological Chemistry, 2002, pp. 22896-22901, vol. 277, No. 25.

Mezey et al., Distribution of mRNA for vanilloid receptor subtype 1 (VR1), and VR1-like immunoreactivity, in the central nervous system of the rat and human, PNAS, 2000, pp. 3655-3660, vol. 97, No. 7.

Miyawaki et al, Dynamic and quantitative Ca2+ measurements using improved cameleons, Proc. Natl. Acad. Sci. USA,1999, pp. 2135-2140, vol. 96, No. 5.

Nagai et al, Circularly permuted green fluorescent proteins engineered to sense Ca2+, PNAS, 2001, pp. 3197-3202, vol. 98, No. 6.

Newbolt et al., Membrane Topology of an ATP-gated Ion Channel (P2X Receptor), The Journal of Biological Chemistry, 1998, pp. 15177-15182, vol. 273, No. 24.

North, Molecular Physiology of P2X Receptors, Physiol Rev., 2002, pp. 1013-1067, vol. 82, No. 4.

Peterlin et al., Optical probing of neuronal circuits with calcium indicators, PNAS, 2000, pp. 3619-3624, vol. 97, No. 7.

Sakai et al., Inducible and Brain Region-Specific CREB Transgenic Mice, Molecular Pharmacology, 2002, pp. 1453-1464, vol. 61, No. 6.

Sandberg et al., Regional and strain-specific gene expression mapping in the adult mouse brain, PNAS, 2000, pp. 11038-11043, vol. 97, No. 20.

Shah et al., Engineering unnatural nucleotide specificity for Rous sarcoma virus tyrosine kinase to uniquely label its direct substrates, Proc. Natl. Acad. Sci. USA, 1997, pp. 3565-3570, vol. 94, No. 8.

Takamori et al., Identification of Differentiation-Associated Brain-Specific Phosphate Transporter as a Second Vesicular Glutamate Transporter (VGLUT2)., The Journal of Neuroscience, 2001, pp. RC182, vol. 21, No. 22.

Vallier et al., An efficient system for conditional gene expression in embryonic stem cells and in their in vitro and in vivo differentiated derivatives, PNAS, 2001, pp. 2467-2472, vol. 98, No. 5.

Zambrowicz et al., Disruption of overlapping transcripts in the ROS βgeo 26 gene trap strain leads to βgeo widespread expression of β-galactosidase in mouse embryos and hematopoietic cells, Proc. Natl. Acad. Sci. USA, 1997, pp. 3789-3794, vol. 94, No. 8.

Zemelman et al., Photochemical gating of heterologous ion channels: Remote control over genetically designated populations of neurons, PNAS; 2003, pp. 1352-1357, vol. 100, No. 3.

Fleming J et al. "Adeno-associated virus and lentivirus vectors mediate efficient and sustained transduction of cultured mouse and human dorsal root ganglia sensory neurons." Human Gene Therapy. 2001. pp. 77-86. vol. 12, No. 1.

Kawashima E et al. "A novel and efficient method for the stable expression of heteromeric ion channels in mammalian cells." Receptors & Channels. 1998. pp. 53-60. vol. 5, No. 2.

Lynch K J et al. "Molecular and functional characterization of human P2X(2) receptors." Molecular Pharmacology. 1999. pp. 1171-1181. vol. 56, No. 6.

McIntyre P et al. "Pharmacological differences between the human and rat vanilloid receptor 1 (VR1)." British Journal of Pharmacology. 2001. pp. 1084-1094. vol. 132, No. 5.

Renard S et al. "Development of an inducible NMDA receptor stable cell line with an intracellular Ca2+ reporter." European Journal of Pharmacology. 1999. pp. 319-328. vol. 366, No. 2-3.

Trouet D et al. "Use of bicistronic GFP-expression vector to characterise ion channels after transfection in mammalian cells." European Journal of Physiology. 1997. pp. 632-638. vol. 434, No. 5.

Utomo Ahmad R H et al. "Temporal spatial, and cell type-specific control of Cre-mediated DNA recombination in transgenic mice." Nature Biotechnology, Nature Publishing Group. 1999. pp. 1091-1096. vol. 17, No. 11.

* cited by examiner

Fig. 5A
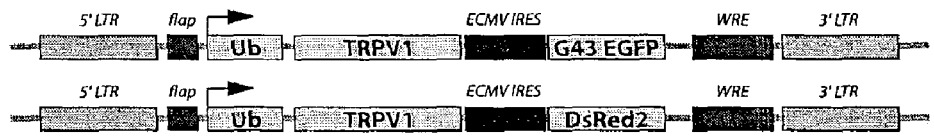

Fig. 5B
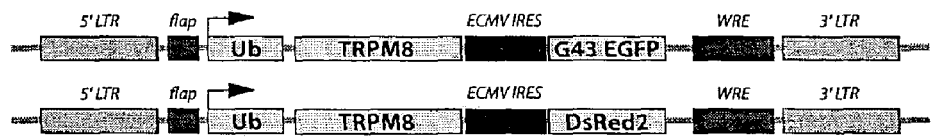

Fig. 5C
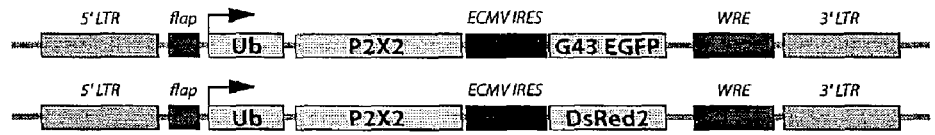

Fig. 5D
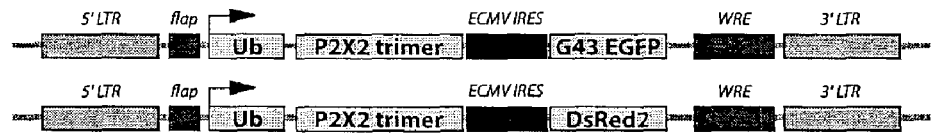

Genes:

| | |
|---|---|
| TRPV1 | TRPV1 gene |
| TRPM8 | TRPM8 gene |
| $P2X_2$ | P2X gene |
| $P2X_2$ trimer | P2X gene cloned as a covalent trimer |
| G43 EGFP | Enhanced green fluorescent protein fused to membrane anchoring signal of growth-associated protein-43 |
| DsRed2 | Red fluorescent protein |

Regulatory and structural elements:

| | |
|---|---|
| flap | HIV-1 central DNA flap for efficient nuclear import |
| WRE | Woodchuck hepatitis virus posttranscriptional regulatory element |
| ECMV IRES | Encephalomyocarditis virus internal ribosome entry site |
| Ub | Ubiquitin promoter |
| 5' LTR | Long terminal repeat from the HIV-1 viral genome includes cytomegalovirus immediate early gene promoter |
| 3' LTR | Long terminal repeat from the HIV-1 viral genome |

Fig. 6A 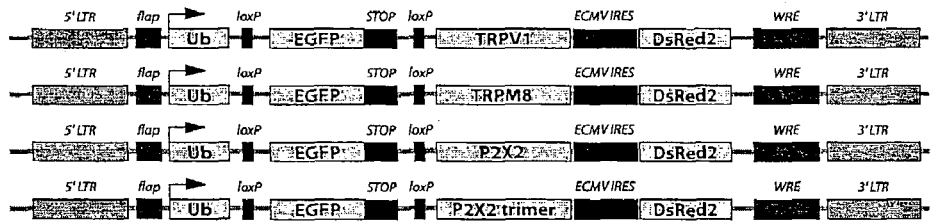

Fig. 6B 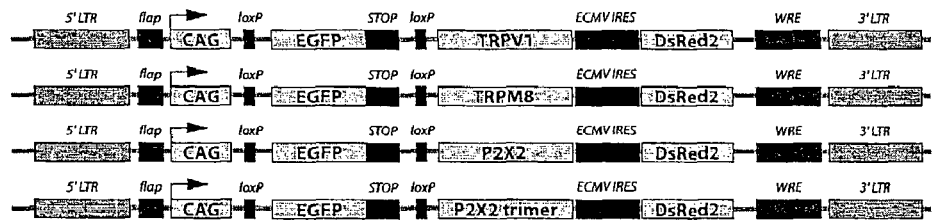

Fig. 6C 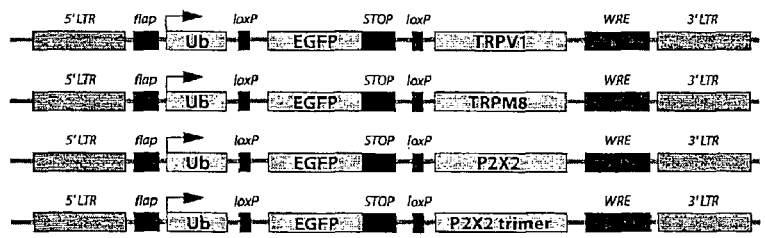

Fig. 6D 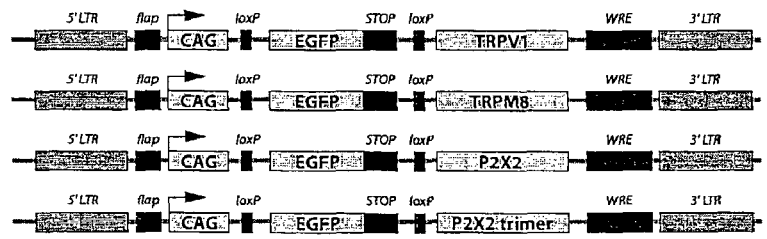

Genes:

| | |
|---|---|
| TRPV1 | TRPV1 gene |
| TRPM8 | TRPM8 gene |
| $P2X_2$ | P2X gene |
| $P2X_2$ trimer | P2X gene cloned as a covalent trimer |
| EGFP | Enhanced green fluorescent protein |
| DsRed2 | Red fluorescent protein |

Regulatory and structural elements:

| | |
|---|---|
| flap | HIV-1 central DNA flap for efficient nuclear import |
| WRE | Woodchuck hepatitis virus posttranscriptional regulatory element |
| loxP | Bacteriophage P1 Cre recombinase target sequence |
| ECMV IRES | Encephalomyocarditis virus internal ribosome entry site |
| STOP | Translation terminator in all three reading frames |
| Ub | Ubiquitin promoter |
| CAG | Chicken β-actin promoter |
| 5'LTR | Long terminal repeat from the HIV-1 viral genome includes cytomegalovirus immediate early gene promoter |
| 3'LTR | Long terminal repeat from the HIV-1 viral genome |

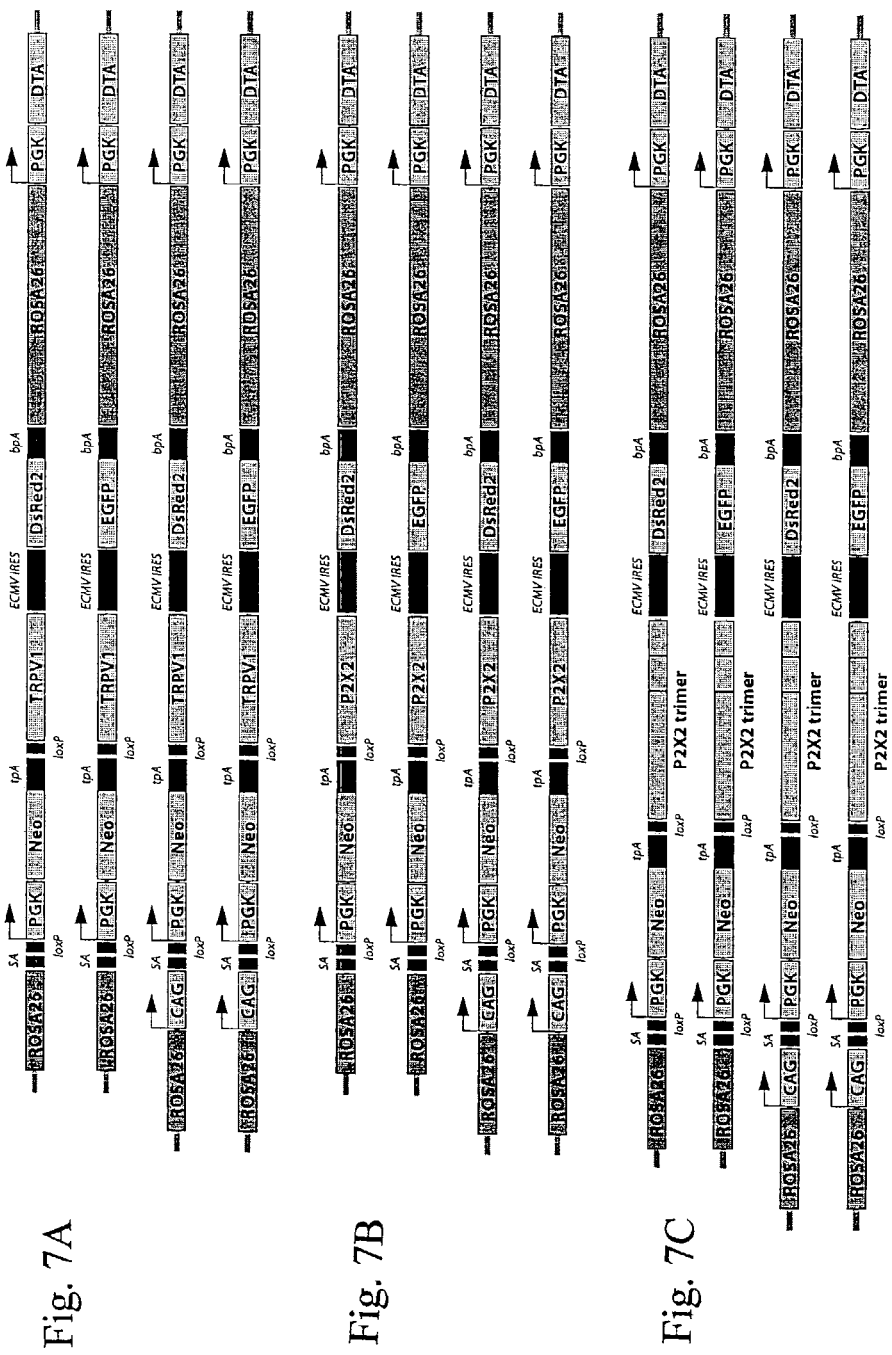

HETEROLOGOUS STIMULUS-GATED ION CHANNELS AND METHODS OF USING SAME

This application claims the benefit of U.S. Provisional Applications Nos. 60/384,670, filed May 31, 2002 and 60/441,452, filed Jan. 21, 2003, which are incorporated herein by reference.

BACKGROUND OF THE INVENTION

This application relates to heterologous stimulus-gated ion channels, and to the triggering of such channels, when expressed in cells, to selectively activate those cells.

The activation of a cell is defined as a shift in the electrical potential across the plasma membrane of the cell from a resting (or polarized) value to an excited (or depolarized) value, or as an increase in the intracellular concentration of calcium ion from a resting (or basal) value to an elevated value. Cellular activation via membrane potential shifts underlies, for example, neuronal activity; sensory transduction; the contraction of skeletal, cardiac, and smooth muscle; and glucose sensing by beta-cells of the pancreas. Cellular activation via increases in the concentration of calcium ion underlies, for example, exocrine, endocrine, and paracrine secretion; chemical neurotransmission; the contraction of skeletal, cardiac, and smooth muscle; cell death; and T-cell activation. Being able to regulate any or all of these processes selectively has important implications for biological research, drug discovery, and medicine.

Mechanistically, the activation of a cell is effected by transmembrane ion channels whose conducting pores open and close (are "gated") in response to physical or chemical stimuli. Known physical stimuli that gate ion channels include changes in membrane potential (voltage-gated channels), mechanical stress (mechanosensitive channels), or temperature (temperature-sensitive channels). Known chemical stimuli that gate ion channels include changes in the concentrations of intracellular messengers (e.g., calcium- and cyclic-nucleotide-gated channels) or extracellular signaling molecules (e.g., ionotropic neurotransmitter receptors).

SUMMARY OF THE INVENTION

The invention provides methods and compositions to activate a genetically designated target cell (or population of target cells) artificially, in vivo or in vitro. The method employs triggering of heterologous stimulus-gated ion channels to activate the cells. The stimulus-gated ion channels are suitably TRPV1, TRPM8 or $P2X_2$. A stimulus which leads to opening or "gating" of the ion channel can be a physical stimulus or a chemical stimulus. Physical stimuli can be provided by heat, or mechanical force, while chemical stimuli can suitably be a ligand, such as capsaicin for TRPV1 or ATP for $P2X_2$, or a "caged ligand," for example a photolabile ligand derivative, in which case a physical signal in the form of light is used to provide the chemical signal.

The invention provides methods for producing genetically engineered animals, preferably mice, whose cells or groups of cells express the stimulus-gated ion channels and, therefore, can be activated by physical stimuli or chemical ligands specific for those channels. Such animals can be knock-in, transgenic, or non-transgenic animals, whose cells express the stimulus-gated ion channels transiently.

The invention provides methods for activating cells expressing the heterologous stimulus-gated ion channels in genetically engineered animals or in explanted tissues derived from these animals. The invention also provides methods for activating transfected or infected cells expressing heterologous stimulus-gated ion channels in explanted tissues or cell cultures. Furthermore, the invention provides methods for monitoring the morphological, physiological, biochemical, and genetic effects of any such cellular activation.

The invention provides methods for mapping neuronal pathways by activating specific cells and monitoring the response of downstream cells within an explanted tissue or animal. Such pathways may include neurotransmitter pathways, cell signaling pathways, and neuronal circuits.

The invention provides methods for identifying novel neuronal pathways by activating neuronal cells at random and monitoring the response of downstream cells within an explanted tissue or animal. Such pathways may include neurotransmitter pathways, cell signaling pathways, known neuronal circuits and previously unknown neuronal circuits.

The invention provides methods for identifying cells whose activation leads to a particular physiological, behavioral, or disease state. The invention further provides methods for identifying cells whose activation leads to the alleviation of particular physiological, behavioral, or disease state or response. Such states or responses may include exocrine, endocrine, and paracrine secretion; the contraction of skeletal, cardiac, and smooth muscle; glucose sensing by beta-cells of the pancreas, cell death, and T-cell activation; sensation and perception of pain, movement, sexual behavior, reward-seeking and addiction, attention, aggression, depression, sleeping, feeding, fasting, cognition, emotion, learning, memory, homeostasis, and others.

The invention provides methods for making use of activated cells in knock-in, transgenic, or non-transgenic non-human organisms and explanted tissue from such organisms in the identification and isolation of pure populations of particular types of cells. The invention further provides such isolated cells. Such cells can be, for example, derived from a particular eukaryotic tissue or region of tissue. The eukaryotic cells or tissues are preferably mammalian, for example mouse, rat or human, but may also be of other types, including, but without limitation, C. elegans, zebrafish or Drosophila. The invention further provides methods of using such isolated cells in assays, such as drug screening assays, pharmacological, biochemical, physiological, morphological, and gene expression assays. The isolated cells can be expressing the stimulus-gated ion channels or they can be unmodified cells of the same type. The cells expressing the stimulus-gated ion channels can, furthermore, be in the stimulated or unstimulated state.

The invention provides novel modified ("caged") ligands that can be used with the stimulus-gated ion channels. The modification consists of a photo-labile group that is attached via a photolabile bond to the ligand, making the ligand inactive until uncaged by light. Specifically, the invention provides the modified (caged) capsaicin. Additionally, the invention provides methods for caging other chemical ligands, including menthol and icilin, thereby making them inactive until uncaged by light.

The invention provides methods for stimulating the stimulus-gated ion channels at a selected moment and/or repeatedly, at selected intervals, using the caged ligands. Further, the invention provides methods for stimulating the stimulus-gated ion channels at a selected location within a eukaryotic organism or tissues of such organism. Specifically, the invention provides methods for stimulating the ion channels by uncaging the caged ligands using light at a chosen moment or location, thereby liberating functional ligand and activating the proximate cells or groups of cells expressing those ion channels.

The invention provides expression units useful for introducing the heterologous stimulus-gated ion channels into the cells of non-human organisms. Such expression units are able to limit the expression of stimulus-gated ion channels to certain designated types or classes of cells; the expression units can also provide control over the timing or the stage in an organism's development during which the stimulus-gated ion channels are to be expressed.

The invention further provides expression units useful in introducing the heterologous stimulus-gated ion channels into human cells for the purpose of treating particular physiological, behavioral, or disease states or responses in humans through gene therapy.

BRIEF DESCRIPTION OF THE DRAWINGS

FIG. 5 shows lentiviral bicistronic vectors encoding the indicated ion channel genes and used for infecting cultured eukaryotic cells and tissues, for injection into tissues, and for generating transgenic animals. The vectors encode a fluorescent protein to aid in identifying and tracking infected cells.

FIG. 6 shows lentiviral monocistronic and bicistronic vectors encoding the indicated ion channel genes and used for generating transgenic animals. Between the promoter and the ion channel gene each vector contains a translation stop in three reading frames flanked by loxP sequences, preventing the expression of the ion channel unless the bacterial Cre recombinase is expressed in the same cell. The requirement for the Cre protein allows cells that express the ion channels to be precisely specified. To mark infected cells and to provide a reliable indicator of successful stop cassette deletion, a fluorescent protein is also encoded between the loxP sites.

FIG. 7 shows ROSA26 genomic targeting vectors. The vectors encode a genomic copy of one ion channel gene (and a covalent trimer, in the case of P2X$_2$) and a fluorescent protein for tracking cells that express the ion channels in a bicistronic cassette. Between the endogenous ROSA26 promoter or the heterologous CAG promoter each vector contains a transcriptional stop sequence flanked by loxP sequences, preventing the expression of the ion channel unless the bacterial Cre recombinase is expressed in the same cell. The requirement for the Cre protein allows cells that express the ion channels to be precisely specified. The vectors also include the Neo gene for selection of stable integrants using G418 and the diphtheria toxin gene for selecting against non-homologous integrants.

DETAILED DESCRIPTION OF THE INVENTION

Figure 1:
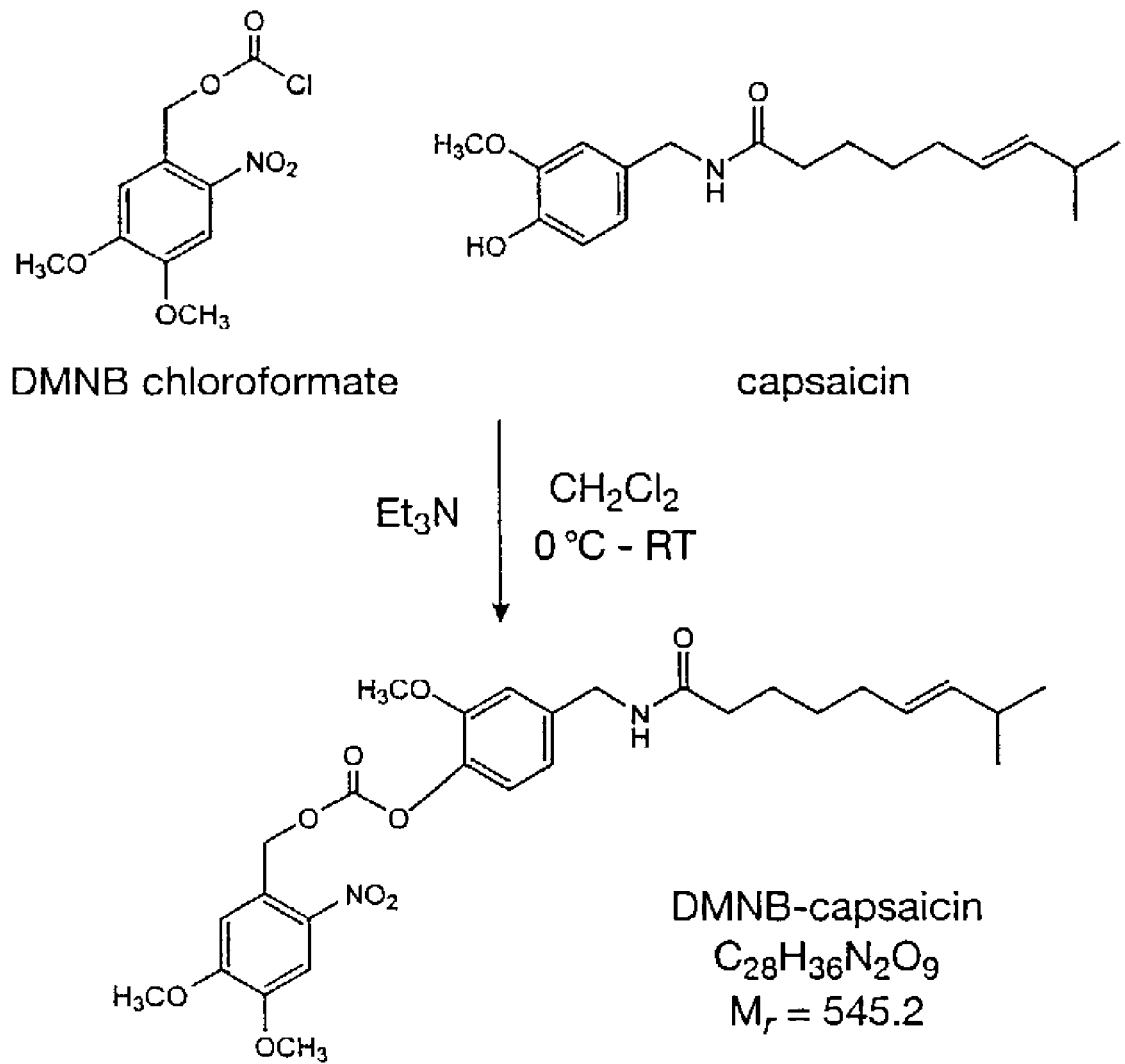
FIG. 1 shows a reaction scheme for the preparation of DMNB-capsaicin.

The present invention provides a method for activating eukaryotic cells that employs triggering of heterologous stimulus-gated ion channels to sensitize the cells. As used in this application, the term "cells" refers to living cells in cell culture, in explanted organs or structures and to cells in a living organism. The eukaryotic cells are preferably mammalian, for example mouse, rat or human, but may also be of other types, including without limitation *C. elegans*, zebrafish or Drosophila.

The present invention provides a methodology for utilization of heterologous stimulus-gated ion channels in a variety of applications, utilizing ion channels that are directly triggered by a selectively controllable stimulus at the time and place of choice by application of the stimulus. In the specification and claims of this application, the term "applying a stimulus" refers to the application by human intervention of a stimulus that is not present in the absence of such intervention in the normal environment of a given transduced cell. Thus, the stimulus may be exposure to a chemical ligand that is not normally present, i.e., that are not normally present at the levels required for observable stimulation, or a physical stimulus which is not normally present, such as localized heating or cooling. The invention therefore is different from methods such as that disclosed in U.S. Pat. No. 6,548,272 and the corresponding PCT publication WO 00/06289, which describe a screening procedure for evaluating drugs that interact with intrinsic or heterologous ion channels, such as for example a calcium channel encoded by the HIV-1 genome. The present invention, in contrast, uses heterologous stimulus-gated ion channels and their cognate stimuli as tools for activating cells artificially, and describes screening procedures for evaluating drugs that affect the activity of specific cell types or the consequences of such activity, rather than interactions of the drugs with the heterologous ion channels themselves.

As used in this application, the terms "activate" or "activation" (or in some instances "sensitize" or "sensitization") refer to inducing a specific response from the cell upon triggering of the ion channel. In a neuronal cell, this response may be polarization and/or depolarization. In other cells, the response may be commencement or termination of secretion, elevation of intracellular $Ca^{2+}$ concentration, contraction or relaxation (i.e., in a muscle or other contractile cells), or a sensory response.

As used in the present application, the term "heterologous stimulus-gated ion channel" refers to a transmembrane ion channel which is expressed in a cell to be activated, and which is directly triggered by a selectively controllable stimulus, either in the form of a physical stimulus, such as heat, or a chemical stimulus, such as binding of a ligand to the channel. The channel can be expressed on the plasma membrane of the cell and/or on the membrane of an intracellular compartment, such as the endoplasmic reticulum (ER) (Liu, Liu et al. 2003; Marshall, Owen et al. 2003).

As used in the present application, the term "to trigger" refers to the opening of the channel following physical or chemical stimulation to allow ions to pass passively through the channel from a region of higher ion concentration to a region of lower concentration. In the case of calcium, the ions can pass across the plasma membrane into the cytoplasm or from an intracellular compartment, such as the ER, into the cytoplasm.

A stimulus-gated ion channel is considered "heterologous" if it is introduced into the cells through human intervention. The ion channel may be from the same species as the target cell or from a different species. Preferably, the heterologous stimulus-gated ion channel is also one that does not naturally occur in the cell in the absence of human intervention. For example, the ion channel may be modified through the alteration of its amino acid composition to be triggered by a foreign or man-made ligand, or different physical stimulus—such as a higher or lower temperature—than would normally be required. Stimulus-gated ion channels are preferably selected for use in the present invention by application of the following seven criteria. The ideal channel would (i) carry a current of suitable polarity and/or ionic composition and (ii) be gated directly by a physical stimulus, such as light, heat, mechanical force, or by a small, drug-like chemical agonist that is (iii) not used as a neurotransmitter in the central nervous system (particularly where the cell to be activated is a neuronal cell). The channel's (iv) non- or slowly desensitizing conductance would be formed by a (v) monomeric or homo-oligomeric protein whose (vi) subunits contain an even number of transmembrane segments. This transmembrane topology ensures that both termini of the channel polypeptide emerge on the same side of the plasma membrane, allowing subunits to be linked covalently into multimers to prevent subunit mixing with endogenous channels. (vii) Finally, the channel would be gated by an agonist that can be derivatized with photolabile blocking groups ("cages") that render the molecule biologically inert. Cells can then be stimulated either pharmacologically, through direct application of agonist, or indirectly, for example optically, through photorelease of agonist from a caged precursor.

Figure 9:
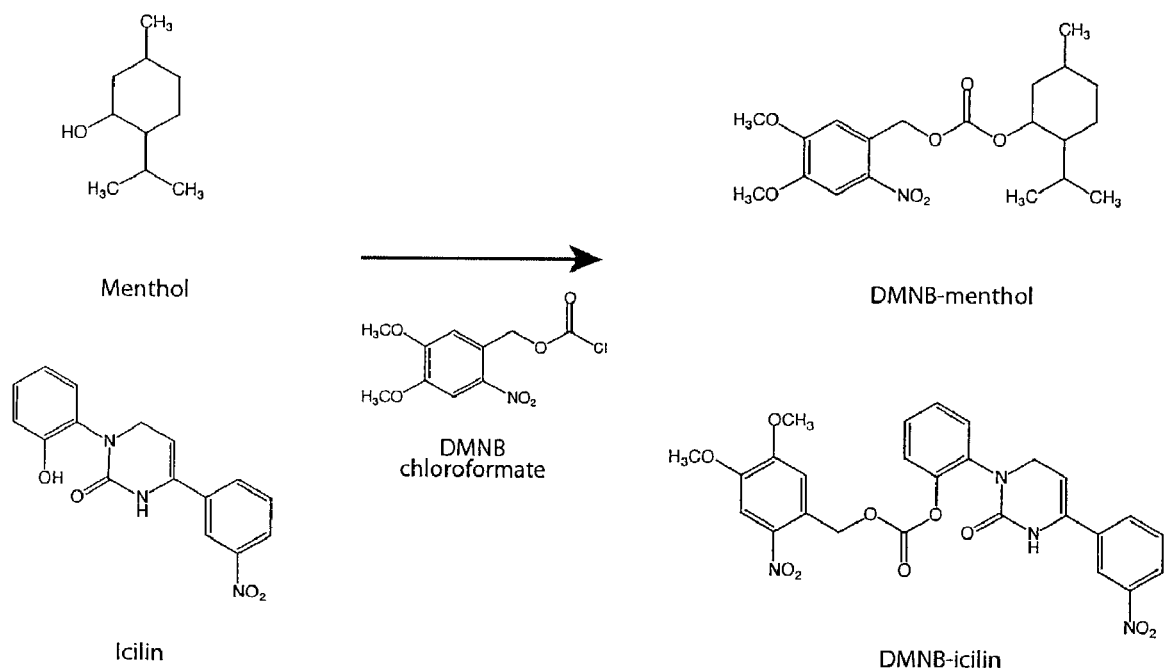
FIG. 9 shows the chemical structures of menthol and icilin caged according to the methods provided herein.

TRPV1 and TRPM8, the vanilloid and menthol receptors expressed by nociceptive neurons of the peripheral nervous system (Caterina, Schumacher et al. 1997; McKemy, Neuhausser et al. 2002; Peier, Moqrich et al. 2002), match this filter almost perfectly. Both channels and their principal agonists—capsaicin and cooling compounds, such as menthol, respectively—are virtually absent from the central nervous system (Caterina, Schumacher et al. 1997; McKemy, Neuhausser et al. 2002; Peier, Moqrich et al. 2002), but see also Mezey (Mezey, Toth et al. 2000). Both channels are thought to function as non-selective, sodium- and calcium-permeable homotetramers (Caterina, Schumacher et al. 1997; Clapham, Runnels et al. 2001; McKemy, Neuhausser et al. 2002; Montell, Birnbaumer et al. 2002; Peier, Moqrich et al. 2002). Both can be triggered by changes in temperature as well as chemical ligand binding. Finally, capsaicin and some cooling compounds, including menthol and icilin, contain potential acceptor sites for photolabile blocking groups (FIG. 9). Association of a photolabile blocking group with such an acceptor would result in a stimulus-gated ion channel in which light acts as an indirect trigger by releasing the active ligand.

$P2X_2$, an ATP-gated non-selective cation channel (Brake, Wagenbach et al. 1994; Valera, Hussy et al. 1994) distinguished by its slow rate of desensitization (Ding and Sachs 2000; North 2002), represents a candidate from a channel family other than the TRP superfamily of ion channels. The utility of $P2X_2$ as a selectively addressable source of depolarizing current may be limited to some extent by the presence of endogenous purinergic receptors at some central synapses (Brake, Wagenbach et al. 1994; Valera, Hussy et al. 1994; Brake and Julius 1996; North 2002). Nevertheless, $P2X_2$ presents an ideal platform for the generation of engineered channel-ligand combinations that lack natural agonists altogether.

ATP-gated ion channels like $P2X_2$ possess one of the simplest known channel architectures (Brake, Wagenbach et al. 1994; Valera, Hussy et al. 1994; Brake and Julius 1996; Hille 2001; North 2002) and a large extracellular ligand-binding domain (Brake, Wagenbach et al. 1994; Valera, Hussy et al. 1994; Newbolt, Stoop et al. 1998; North 2002) whose atomic structure might be determined with relative ease. A high-resolution structure can be used to guide the design of mutations in the channel's ligand-binding domain that abolish sensitivity to ATP (Shah, Liu et al. 1997; Bishop, Buzko et al. 2000). "Second-site" substitutions on the nucleotide ligand (Shah, Liu et al. 1997; Bishop, Buzko et al. 2000) can complement these mutations and restore functional (but entirely unnatural) receptor-ligand pairs. Less targeted, or even random mutations could also be used to create mutant species lacking affinity for the natural agonist. Libraries of potential agonist compounds can then be screened to identify useful non-natural agonists. Similar chemical genetic approaches are also useful for altering the conducting properties of the ion channel, such as ion selectivity.

Chemical genetic approaches are useful for altering the ligand binding, physical activation properties, or conducting properties of heterologous stimulus-gated ion channels. For example, mutant channels can be selected for the ability to conduct potassium ions instead of sodium or calcium ions. When expressed in neurons and triggered by a physical or chemical stimulus, such mutant ion channels would hyperpolarize and inactivate the neurons.

The genetic sequences for TRPV1, TRPM8 and $P2X_2$ are known in the art, for example from Caterina, et al. (Caterina, Schumacher et al. 1997), McKemy (McKemy, Neuhausser et al. 2002), Valera, et al., (Valera, Hussy et al. 1994), and Brake, et al.,(Brake, Wagenbach et al. 1994). The sequences are also listed under GenBank Accession Nos AF029310, NM134371 and NM053656 and are attached hereto (Seq. ID Nos: 1, 2 and 3).

TRPV1, TRPM8 and $P2X_2$ are members of large families of ion channels that share structural features as well as gating principles. For example TRPV4, similar to TRPV1, is also triggered by heat, but not by capsaicin (Guler, Lee et al. 2002). $P2X_3$, moreover, is triggered by ATP, as is $P2X_2$, but desensitizes more rapidly (North 2002). The present invention anticipates the use of individual ion channel genes to form homo-oligomeric channels in target cells as well as combinations of ion channel genes to form mixed, hetero-oligomeric channels with novel properties (North 2002), as required by the specific biological application. TRPV1, TRPM8 and $P2X_2$ are, therefore, non-limiting examples.

In order to activate cells in accordance with the invention, a genetic sequence encoding a heterologous stimulus-gated ion channel is introduced into and expressed in a target cell population. This introduction can take the form of "knock-in" animals, preferably mice, where a knock-in structure, in which a genetic sequence encoding a heterologous stimulus-gated ion channel is inserted by homologous replacement into a specific locus, such as the ROSA26 locus (Zambrowicz, Imamoto et al. 1997; Soriano 1999), within the animal's genome, disrupting, eliminating, or trailing an endogenous sequence whose expression pattern is known; expression of the genetic sequence encoding the heterologous stimulus-gated ion channel may then be under the control of the promoter responsible for the expression of the endogenous gene, as is the case for the ROSA26 locus (Zambrowicz, Imamoto et al. 1997; Soriano 1999; Awatramani, Soriano et al. 2001), and substantially resemble the expression pattern of that endogenous gene. Where the stimulus-gated ion channel gene is inserted into the genome after the termination codon of the endogenous gene, the stimulus-gated ion channel gene must be preceded by an internal ribosome entry site (IRES), such as the ECMV (encephalomycarditis virus) IRES (Jang, Krausslich et al. 1988; Jackson, Howell et al. 1990). Alternatively, the stimulus-gated ion channel gene operationally linked to a heterologous promoter can be inserted by homologous replacement into the animal's genome disrupting, eliminating or trailing an endogenous sequence; expression of the genetic sequence encoding the heterologous stimulus-gated ion channel may then be under the control of the heterologous promoter and substantially resemble the expression pattern of a gene operationally linked to this promoter in a non-transgenic animal. Alternatively, a stimulus-gated ion channel gene and a heterologous promoter to which it is operationally linked can be randomly (non-homologously) inserted into the host's genome, creating a "transgenic" animal; expression of the genetic sequence encoding the heterologous stimulus-gated ion channel may then be under the control of the heterologous promoter and substantially resemble the expression pattern of a gene operationally linked to this promoter in a non-transgenic animal. Alternatively, a stimulus-gated ion channel gene lacking a promoter can be randomly (non-homologously) inserted into the host's genome; expression of the genetic sequence encoding the heterologous stimulus-gated ion channel may then be under the control of a promoter near the insertion site and substantially resemble the expression pattern of an endogenous gene near the insertion site. Alternatively, a stimulus-gated ion channel gene and a heterologous promoter to which it is operationally linked can be introduced in a viral or other vector. Examples of lentivirus vectors that may be used for this purpose are provided below. (For an overview of methods for generating transgenic animals and controling transgene expression see Houdebine (Houdebine 2002).)

In all these cases, depending on the application, limiting the expression of the heterologous stimulus-gated ion channel to certain defined cell type(s) depends on the use of a cell specific or tissue specific promoter that inherently possesses the desired specificity. Examples of such promoters include the following: the promoter for GABA decarboxylase (Makinae, Kobayashi et al. 2000), which is specific for inhibitory neurons; the promoter/enhancer for Wnt-1 and the endothelin receptor B promoter (Zinyk, Mercer et al. 1998; Jiang, Rowitch et al. 2000), both of which are specific for the mouse neural crest; vesicular glutamate transporter promoter (Takamori, Rhee et al. 2001); calbindin promoter specific for the Purkinje cells of the cerebellum (Arnold and Heintz 1997); a 2 kb promoter for synaptic vesicle protein synapsin 1, which has been used to express transgenes in neuroblastoma and other neuronal cell lines, but not in non-neuronal cell lines (Kugler, Meyn et al. 2001); platelet-derived growth factor B-chain (PDGF B) promoter, which has been used to preferentially target neurons in the cortex, cerebellum and hippocampus (Georgopoulos, McKee et al. 2002; Rockenstein, Mallory et al. 2002); a 1.8 kb neuron-specific enolase (NSE) promoter, which has been used to express transgenes in mouse retina and spinal cord (Sakai, Thome et al. 2002); 2.9 kb of upstream non-coding DNA from the myosin heavy chain gene (MHC promoter/enhance), which has been used to direct transgene expression in the mouse heart (Matsui, Li et al. 2002); 1.6 kb of retinoblastoma gene (RB) promoter, which has been used to label the retinal ganglion cell layer, neurons of the cerebellum, glial cells of the thalamus and myocytes in the thigh muscle (Jiang, Guo et al. 2001); 0.9 kb of whey acidic protein (WAP) promoter, which has been used to target mammary epithelial cells (Ozturk-Winder, Renner et al. 2002); 8.5 kb of Ca2+-calmodulin-dependent protein kinase II subunit (CaMKII) promoter, which has been used to express transgenes in the mouse hippocampus, cortex, cerebellum and olfactory bulb (Jerecic, Schulze et al. 2001); glucagon (Gcg) promoter, which has been used to express human growth hormone in the pancreatic islets (Yamaoka, Yoshino et al. 2002); insulin (Ins2) promoter, which has been used to express human growth hormone in the b-cell of the pancreas (Herrera 2000); Myh6 promoter, which is specific for mouse heart cells (Lee, Morley et al. 1998); Lap promoter, which is specific for mouse liver cells (Lavon, Goldberg et al. 2000); and Fabp promoter, which is specific for mouse small intestine cells (Saam and Gordon 1999).

Additional promoters, as well as techniques for identifying promoters specific for particular cell types and/or two-component gene expression systems (involving, for example, transcriptional transactivation or site-specific DNA recombination) are disclosed in DeFalco et al., (DeFalco, Tomishima et al. 2001); Zemelman et al., (Zemelman and Miesenböck 2001); Sandberg et al., (Sandberg, Yasuda et al. 2000); Lewandoski, (Lewandoski 2001); and Stanford et al., (Stanford, Cohn et al. 2001).

An alternative to the use of a cell-type specific promoter is the use of a multi-component expression system, which provides cell-type specificity, such as the Cre-lox system. (Hoess and Abremski 1984; Hoess and Abremski 1985). In the Cre-lox system, a general promoter (one that supports gene expression throughout the animal) is employed, but it is separated from the genetic sequence encoding, for example, the heterologous stimulus-gated ion channel by a loxP-stop-loxP region, such that expression does not ordinarily occur. The "stop" sequence can be either a transcription or a translation "stop" sequence. A second sequence is then introduced containing a genetic sequence encoding the bacterial Cre protein operationally linked to a cell specific or tissue specific promoter. When that Cre protein is expressed in a defined subset of cells, it acts to excise the stop sequence between the loxP sites, and thus activates expression of the heterologous gene, such as the stimulus-gated ion channel gene, in those cells. The introduction of the second DNA sequence into the transgenic or knock-in animal with the loxP-stop-loxP cassette and linked to a general promoter can be done transiently with a virus or with another vector. Alternatively, two transgenic or knock-in animals can be mated so that the progeny will have the loxP-stop-loxP cassette in all cells (from parent 1) and the Cre to excise the stop in a subset of those cells (from parent 2) resulting in a defined expression pattern of the heterologous gene, such as the stimulus-gated ion channel gene (for an example of this methodology see Srinivas (Srinivas, Watanabe et al. 2001)).

The expression of the heterologous stimulus-gated ion channel can also be controlled temporally using an inducible promoter, i.e, one that can be turned on and off at selected times in response to external signals. Such promoters are known that respond to steroids, antibiotics, 4-OH tamoxifen, and heavy metals (Hofmann, Russell et al. 1988; Lewandoski 2001; Vallier, Mancip et al. 2001; Bex, Vooijs et al. 2002; Gossen and Bujard 2002; Roscilli, Rinaudo et al. 2002).

For purposes of introducing heterologous stimulus-gated ion channels using a vector, the invention provides useful expression units. As used in this application, the term "expression units" refers to viral vectors, plasmids and the like which provide for expression of a heterologous protein or peptide encoded by the expression unit. This expression can occur when the expression unit is integrated into the genome of a target cell or directly from the expression unit. Each expression unit comprises a sequence encoding a functional stimulus-gated ion channel; and promoter effective to result in expression of the ion channel in the target cells, and cell-type specific and/or temporal expression control elements. The expression control elements may be the same as or in addition to the promoter, and are effective to limit the expression of the ion channel except in cells of a specific type or character and/or at the designated time. Examples of cell type specific promoters and other control elements are discussed above.

The expression units of the invention may also contain additional sequences. For example, in the plasmids discussed below, the plasmids carry two genes in tandem: the first encoding a stimulus-gated ion channel (TRPV1 (Caterina and Julius 2001), TRPM8 (McKemy, Neuhausser et al. 2002), or P2X$_2$ (Valera, Hussy et al. 1994)) and operationally linked to a promoter and appropriate expression control elements, and the second encoding GAP43-EGFP (a membrane-associated enhanced green fluorescent protein) (Moriyoshi, Richards et al. 1996), acting as a transfection marker, preceded by an IRES (internal ribosome entry site). Such transfection markers (e.g., fluorescent proteins including GFP, EGFP, DsRed, DsRed2 or enzymes including lacZ and beta-lactamase) are not needed for the function of the heterologous stimulus-gated ion-channel in the selective activation of cells, but are convenient for confirming the extent of transfection and heterologous protein expression and for other purposes, including the ability to find and isolate sensitized cells by FACS (fluorescence-activated cell sorting), to be used in in vitro applications as discussed below. Other additional sequences that might be incorporated, if desired, include without limitation selection markers which facilitate the selection of transfected cells from a mixed population of transfected and untransfected cells, for example glutamine synthetase, aminoglycoside phosphotransferase, or dihydrofolate reductase, and suicide genes which render the cells susceptible to attack by a specific agent, thus permitting the controlled elimination of transfected cells. Genetically-encoded reporters of cellular activity may also be included in the expression unit. For example, genetic sequences encoding proteins that allow cellular activation to be detected optically are suitably included in the expression unit. Examples include synapto-pHluorin, cameleon, camgaroo, pericam, G-CaMP, and clomeleon. (Miyawaki, Llopis et al. 1997; Miesenböck, DeAngelis et al. 1998; Miyawaki, Griesbeck et al. 1999; Kuner and Augustine 2000; Nagai, Sawano et al. 2001; Nakai, Ohkura et al. 2001; Sankaranarayanan and Ryan 2001; Zemelman and Miesenböck 2001; Shimozono, Fukano et al. 2002).

The general procedures for the introduction of heterologous genetic sequences, either to form knock-in or transgenic animals, preferably mice, are well known and are readily applied to the creation of cells/animals in accordance with the present invention (for review of transgenic methods see Houdebine (Houdebine 2002) and Hogan, et al. (Hogan, Beddington et al. 1994)). These techniques include, without limitation, any method that results in at least transient expression, including without limitation transfection, viral infection and microinjection. Injection of mice with viral vectors to achieve localized gene expression is described in Watson, et al. (Watson, Kobinger et al. 2002), Bainbridge (Bainbridge, Stephens et al. 2001), Gusella (Gusella, Fedorova et al. 2002), and Follenzi, et al. (Follenzi, Sabatino et al. 2002). Collections of mice are known (http://www.mshri.on.ca/nagy/Cre-pub.html) and commercially available in which protein markers or the Cre protein are selectively expressed in cells of different types through the use of cell-type specific promoters. What has been lacking is a method of exploiting this selective expression for activation of specific cell types. The present invention expands upon this utility by allowing the existing cell-type specific expression techniques to be used to place heterologous stimulus-gated ion channels in the already recognized populations of cells. Another benefit of the present invention is that it provides viral vectors, preferably lentiviral vectors pseudotyped with the envelope coat protein of the vesicular stomatitis virus (VSV-G) (Naldini, Blomer et al. 1996; Zufferey, Nagy et al. 1997). These lentiviruses freely infect cells of most mammals. The broad host range of VSV makes it possible to generate transgenic animals of different species, without being limited to mice, as has historically been the case. Furthermore, the VSV coat protein confers sufficient mechanical stability on the virions to permit their concentration in the ultracentrifuge. Alternative pseudotyping options for lentiviral vectors comprise envelope glycoproteins from Ebola virus (Wool-Lewis and Bates 1998), Mokola virus (Mochizuki, Schwartz et al. 1998), lymphocytic choriomeningitis virus (LCMV) (Beyer, Westphal et al. 2002), murine leukemia virus (MuLV) (Kobinger, Weiner et al. 2001), and Ross River virus (RRV) (Kang, Stein et al. 2002). The choice of envelope coat protein affects the types of cells and tissues the resulting virus will infect.

For animal models, introduction of the genetic sequence encoding the heterologous stimulus-gated ion channel can be done in progenitor cells, such that every cell derived from these progenitor cells within the animal will express the stimulus-gated ion channel. Neuronal cells can also be transfected through synaptic contacts. When the appropriate virus (such as herpes simplex virus type I or pseudorabies virus) is used to infect one neuron, the virus spreads through synapses to its neighbors, so that these neurons will then begin to express the stimulus-gated ion channel as well (Lowenstein and Enquist 1996). Where the cell-specific control elements are in the promoter supplied with the genetic sequence, the ion channel will only be expressed in the limited cell population. However, multiple populations of cells within the same animal can be made to express different stimulus-gated ion channels that can be activated independently by mating transgenic or knock-in animals expressing different channels in different populations of cells or by using a viral or other vector to transiently express an additional stimulus-gated ion channel in an animal already expressing one or more channels.

After heterologous expression of a stimulus-gated ion channel is established in an animal using one of the methods listed above, the cells of that animal expressing the stimulus-gated ion channel can be harvested and transplanted into a transgenic, a "knock-in," or a non-transgenic animal by injecting the cells into the embryo of that animal in utero (Nery, Fishell et al. 2002). For this purpose, the expression unit containing the stimulus-gated ion channel would also include a second gene, such as that encoding the enhanced green fluorescent protein (EGFP) gene, which would not be needed for the function of the stimulus-gated channel but would be convenient for isolating and tracking the cells expressing the heterologous stimulus-gated ion channels. Cells isolated from the donor animal based on the detection of EGFP or another expression marker protein are injected into a chosen location within the embryo of a host animal in utero using an ultrasound-guided syringe or another convenient method for identifying the injection site. As the host animal develops, the cells derived from the donor animal are integrated into the host's tissues, leading to the expression of a stimulus-gated ion channel in designated cells and tissues of the host animal.

Cells and animals expressing the heterologous stimulus-gated ion channels in accordance with the invention can be used for a variety of purposes including: (1) for research into activity-dependent morphological, physiological, biochemical, and genetic changes, for example, changes in gene expression, (2) for mapping neuronal pathways, (3) for research into cell-types implicated in different diseases and conditions; (4) in methods for screening compositions for use as additional or alternative therapeutics for treatment of such diseases or conditions; and (5) as part of a therapeutic treatment of such diseases or condition.

In the first embodiment of the invention, the sensitized cells are "normal" cells and morphological, physiological, biochemical, and gene expression changes resulting from the activation of these cells in vivo or in vitro are monitored. Identification of such changes will provide insights into mechanisms of activity-dependent cellular processes, examples of which are enumerated below.

As used in this application, the term "disease or condition" refers to physiological states that differ from the accepted norm regardless of the cause. In general, the diseases or conditions that are of concern are those that have a deleterious impact on the individual with the disease or condition.

In many cases, a defined phenotype is recognized as associated with a disease or condition, but the specific defect giving rise to that disease or condition is not known. Such phenotypes include inappropriate polarization or depolarization, particularly in neuronal cells; particular physiological, behavioral, or disease states or responses. Such states or responses may include exocrine, endocrine, and paracrine secretion; the contraction of skeletal, cardiac, and smooth muscle; glucose sensing by beta-cells of the pancreas, cell death, and T-cell activation; sensation and perception of pain, movement, sexual behavior, reward-seeking and addiction, attention, aggression, depression, sleeping, feeding, fasting, cognition, emotion, learning, memory, homeostasis, and others. The invention provides a method for assessing the cell types involved in a disease or condition comprising the steps of (a) expressing a heterologous stimulus-gated ion channel in the cells of an animal (in vivo) or in explanted tissue or cells derived from the animal (in vitro); (b) triggering the ion channel using a specific stimulus; and (c) observing the effect, if any, of triggering the ion channel and, thereby, activating the cells expressing the ion channel. The animal models discussed above, in which separate groups of cells can be sensitized independently, or in groups, allows greater versatility in that different groups of cells can be activated at different times, to different extents, or in different combinations in the same animal. Also observations can be made before and after the activation of the cells in the same animal so that the effect of each can be clearly seen.

In a second embodiment of this method, the involved cells are "normal" cells, and particularly "normal" animals, that do not display the phenotype of interest. These cells are selectively activated by exposure to the physical or chemical stimulus and the effect which is looked for is the creation of the phenotype associated with the disease or condition. When the phenotype is created, it indicates that the cells expressing the heterologous stimulus-gated ion channel are of significance in a disease or condition, and that they are therefore appropriate therapeutic targets. Therapy might be through the use of a stimulus-gated ion channel, as discussed below, but will more likely be through the development of a specific small molecule agonist chosen for its selective activity relative to the identified class of cells.

In a third embodiment, the involved cells or animals display the phenotype associated with the disease or condition. In this case, one looks for a reduction or elimination of the phenotypic characteristic following activation of a group of cells expressing a heterologous stimulus-gated ion channel. Such a reduction or elimination indicates that the cells expressing the heterologous stimulus-gated ion channel are of significance in a disease or condition, and that they are therefore appropriate therapeutic targets. Again, therapy might be through the use of a stimulus-gated ion channel, as discussed below, but will more likely be through the development of a specific small molecule agonist selected for its selective activity relative to the identified class of cells.

The examples below are intended to illustrate possible applications of the invention and should not be construed as limiting.

In one specific example of the first embodiment of the use of the invention drawn from the field of neurobiology, the artificial activation of a genetically designated neuron (or group of neurons) in explanted neural tissue or an intact nervous system leads to the formation of new dendritic spines or synapses (activity-dependent morphological change), the strengthening of existing synapses (activity-dependent physiological change), or the phosphorylation of neurotransmitter receptors (activity-dependent biochemical change) in the stimulated cells or their synaptic targets. Morphological, physiological, and biochemical changes are expected to correlate with changes in gene expression (activity-dependent genetic change). Gene expression profiling using DNA microarrays can identify activity-regulated genes and provide insights into mechanisms of neuronal growth and branching (important for repair and regeneration), synaptogenesis, and plasticity (important for learning and memory). This implicates these genes and their products as potential drug targets.

In one specific example of the second embodiment of the use of the invention drawn from the field of neurobiology, the artificial activation of a genetically designated neuron (or group of neurons) in explanted neural tissue or an intact nervous system is communicated to all of its downstream synaptic targets. Thus, the method of sensitization of the invention may be used for mapping neuronal pathways. Such a method comprises the steps of (a) sensitizing a cell population in a neuronal pathway, wherein the cell population expresses a heterologus stimulus-gated ion channel; and (b) monitoring the response of putatively downstream cells to the sensitization of the population of cells, wherein observation of response in downstream cells is indicative of the cells are in fact downstream in a neuronal pathway. The sensitization of neuronal cells may be accomplished via any of the methods discussed herein. Monitoring putatively downstream cells is accomplished with a method that depends on the nature of the anticipated response. Changes in the activity of the downstream targets can be detected with the help of methods that are well-known in the art (electrophysiological or optical recordings). However, where the anticipated response is modulation (upwards or downwards) of the secretion of a hormone, the monitoring would appropriately involve detection of hormone levels. The invention thus provides a method to identify and map functional neural circuits, an essential prerequisite for understanding (and interfering with) nervous system function and behavior.

More specifically, the invention may be used to identify and map neurons that participate in the leptin neuronal circuit, affecting obesity and anorexia. The hormone leptin conveys the metabolic state of the body to the brain (Friedman and Halaas 1998; Schwartz, Woods et al. 2000). Secreted into the bloodstream by adipose cells, leptin binds to receptors expressed by neurons within the arcuate nucleus of the hypothalamus, the major integration site for signals related to metabolism and energy balance. A change in the level of leptin alters food intake, metabolism, body temperature, energy consumption, the level of activity, the rate of bone formation, and fertility through pathways conserved among all mammals. Leptin-sensitive neurons signal downstream targets through various neuropeptides, including neuropeptide Y and melanocortins. These act on anabolic and catabolic pathways, whose output neurons are currently unknown. To identify neurons that form the leptin circuit, explanted brain tissue is stimulated with exogenously-added leptin, activating leptin-responsive neurons. Alternatively, the leptin-responsive neurons are activated through expression of stimulus-gated ion channels and the addition of the ligand or application of a physical stimulus able to gate the channels open. In this case, the explanted tissue is derived either from a transgenic or knock-in animal expressing the stimulus-gated ion channels in leptin-responsive cells, a non-transgenic animal treated with a viral or other vector, causing stimulus-gated ion channels to be expressed in the leptin-responsive neurons, or explanted tissue treated with a viral or other vector, causing stimulus-gated ion channels to be expressed in the leptin-responsive neurons. While the leptin-responsive neurons are stimulated, activity is monitored in other neurons within the explanted tissue to identify those neurons whose activity is altered by the leptin-responsive neurons (these neurons are known as downstream synaptic targets of the leptin-responsive neurons). Activity in the downstream synaptic targets of the leptin-responsive neurons may be monitored using electrophysiological recording (Nicolelis and Ribeiro 2002) or optical imaging (Peterlin, Kozloski et al. 2000; Kozloski, Hamzei-Sichani et al. 2001). Alternatively, one may, for example, express genetically encodable optical sensors of neuronal activity listed above (see also Zemelman et al. (Zemelman and Miesenböck 2001)) in some or all of the neurons within the explanted tissue using the techniques described above. One such sensor is called synapto-pHluorin (Miesenböck, De Angelis et al. 1998). Synapto-pHluorins are pH-sensitive mutants of green fluorescent protein ('pHluorins'), developed by structure-directed combinatorial mutagenesis, linked to the lumenal end of a vesicle membrane protein VAMP, placing them inside synaptic vesicles of the neurons before neurotransmitter is released and outside the cell after vesicle degranulation and neurotransmitter release. In the low pH of the vesicle, the pHluorins do not fluoresce. However, after the vesicle fuses with the neuronal plasma membrane, pHluorins end up in the neutral extracellular medium, where they start to fluoresce. The fluorescence is observed under a microscope, pinpointing the neurons whose activity has been altered. The identified neurons are then genetically profiled. This technique, sometimes referred to as SAGE (serial analysis of gene expression), provides a snapshot of the genes active in the neurons of interest (Eberwine, Kacharmina et al. 2001). The information is used in the selection of promoters active in only the identified neurons and to determine what role the neurons play in the brain (Cao and Dulac 2001). Once the promoter information is available, stimulus-gated ion channels are expressed in the newly-identified neurons and their downstream neuronal targets are found using an iteration of the approach just described.

In a second example of the second embodiment, also drawn from the field of neurobiology, the artificial activation of a genetically designated neuron (or group of neurons) in a behaving animal, preferably mouse, leads to alterations in sensation and perception of pain, movement, sexual behavior, reward-seeking and addiction, attention, aggression, depression, sleeping, feeding, fasting, cognition, emotion, learning, memory, homeostasis, and others. These alterations may produce characteristic phenotypes that mimic neurological, psychiatric, or behavioral disorders (Crawley and Paylor 1997; Crawley 1999). The induction of these phenotypes following the artificial activation of the sensitized cells thus implicates these cells as carriers of behaviorally relevant information and potential therapeutic targets. The method not only permits the identification of these potential targets; it creates at the same time a discovery platform using which small molecules can be screened, in vivo or in vitro (using cell or tissue cultures derived from these animals, as described below), for their ability to modulate cellular activation or the resulting behavioral phenotypes. General approaches are outlined in Chart 1 and Chart 2.

Specifically, the present invention may be used, for example, to find novel treatments for obesity and anorexia. Stimulus-gated ion channels are expressed in vivo in downstream target neurons of leptin sensing neurons, as described above, such as proopiomelanocortin (POMC) sensing neurons (Campfield, Smith et al. 1998) using, for example, the same promoter to drive the expression of the stimulus-gated ion channels as is used by the neurons to drive the expression of the POMC receptor. The selected neurons are then stimulated in vivo by supplying the appropriate physical stimulus or ligand using any convenient means, such as injection or uncaging using light, localized heating, or by feeding the animal a pro-drug formulation. The phenotype of the animal after the ligand or other stimulus is supplied is compared to the initial phenotype. Neurons, which when stimulated with ligand cause the animal to lose or gain weight, are then harvested. Because, as described above, DNA vectors encoding the stimulus-gated ion channels also encode a fluorescent protein, the sensitized neurons are also fluorescently labeled. In order to harvest the neurons, animal brains are dissociated into individual cells and the cell suspension is passed through a fluorescence-activated cell sorter (FACS) so that the fluorescently labeled neurons may be separated from the rest (St John, Kell et al. 1986; Tomomura, Rice et al. 2001). These neurons are then exposed in vitro to chemical compounds while their activity is monitored as described above for neurons in explanted tissue. Compounds that activate or silence the neurons in vitro are tested in healthy animals to determine whether or not the animals gain or lose weight. The compounds are also tested in obese and anorexic animals. Compounds that are shown to influence weight regulation are then tested in humans. Alternatively, neurons whose activity is determined to influence weight regulation can be stimulated directly in animals and humans by expressing stimulus-gated ion channels in them using gene therapy (for example, using viral vectors and appropriate promoters) and stimulating them with the specific channel ligands or physical means.

The invention also provides a method for implicating novel neuronal pathways in the regulation of body weight, for example, by sensitizing neurons randomly in vivo using gene trapping (Leighton, Mitchell et al. 2001). Here the DNA sequence for the stimulus-gated ion channel lacking a promoter is inserted randomly through non-homologous recombination into the genomic DNA of stem cells. By chance, in a few of these cells the stimulus-gated ion channel gene inserts near an endogenous neuronal promoter. When the transfected stem cells are used to create transgenic animals, the stimulus-gated ion channel is expressed in a subset of neurons within each animal's brain as determined by each promoter. Because the initial genomic insertions are random, the identities of neuronal cells expressing the stimulus-gated ion channels cannot be known in advance. The insertion point within the genome and the promoter are identified using 5' rapid amplification of complementary DNA ends (5' RACE) and sequencing (Frohman, Dush et al. 1988; Townley, Avery et al. 1997). The neurons are then stimulated in vivo, as previously described, and the resulting phenotype is observed. Neurons, which when stimulated cause the animal to lose or gain weight, are harvested using FACS and genetically profiled, as described above. Chemical compounds are then tested for efficacy on the neurons in vitro and then on healthy and obese and anorexic animals in vivo. Compounds that are shown to influence weight regulation are subsequently tested in humans. Alternatively, neurons whose activity is determined to influence weight regulation can be stimulated directly in animals and humans by expressing stimulus-gated ion channels in those neurons using gene therapy (for example, using viral vectors and appropriate promoters) and stimulating the infected neurons with specific channel ligands or physical means.

Thus, the sensitization approach of the present invention can also be used in a method for screening compositions for use as therapeutics for treatment of diseases and conditions. Once a group of cells is implicated in a disease or condition, either as a result of application of the methods discussed above or from other methodologies, cell lines and animal models are created in which those cells express the heterologous stimulus-gated ion channels, and such that triggering of the ion channel using the appropriate means induces the disease phenotype. Potential therapeutics are screened to assess their ability to treat the phenotype. This methodology offers the advantage of using the same animal in multiple tests. By introducing independently-controllable heterologous stimulus-gated ion channels into a plurality of cell-types and triggering them independently and in combinations, the involvement of the multiple cell types and the efficacy of combined therapies can be assessed in the same animal, thereby reducing experimental variations caused by testing different animals.

Heterologous stimulus-gated ion channels can also be used in therapeutic approaches. Since expression can be limited to the desired cells as described above, and since triggering of the channel can be used to mimic either a disease or alleviate a disease phenotype, therapeutic benefits can be obtained by activating or inhibiting cells associated with a disease or condition or cells that can affect the behavior of the cells associated with a disease or condition. In addition, cells expressing the heterologous stimulus-gated ion channel may be confined within an implant that provides secretion of a therapeutic agent, for example a peptide or protein, in response to the application of the agonist (chemical or physical) stimulus. This stimulus can be made available in response to a signal from an in vivo monitoring system, such as a glucose monitoring system in the case of insulin secretion, to control the availability of the agonist. The ligand, caged or not, or a pro-drug formulation thereof, can also be provided orally or parenterally. Physical stimulation, such as localized heating, cooling, or illumination can also be applied using an implanted device.

One example of a therapeutic approach involves rendering pancreatic islet cells sensitive to stimulation. Islet cells expressing stimulus-gated ion channels are, for example, implanted in a diabetic patient and activated through the application of the appropriate stimulus before a meal or when blood sugar levels are detected by a sensor to rise too high, thereby causing the pancreatic islet cells to secrete insulin. This regimen will eliminate the need to administer insulin parenterally.

Another example of a therapeutic approach involves rendering natural opiate-producing nerve cells sensitive to stimulation. In the patient such cells are infected by a viral vector containing the stimulus-gated ion channels operatively linked to the appropriate promoter as described above. The administration of the stimulus is manually controllable by the patient. In this manner, when the patient desires pain relief, the chemical or physical stimulus is supplied, causing the cells to secrete the endogenous opiate. Such a treatment for pain is expected to be far less addictive than currently prescribed painkillers.

In yet another example of a therapeutic approach utilizing the present invention, there is provided a method of treating incontinence. This method comprises sensitizing those muscle cells involved in bladder control using a viral vector containing the stimulus-gated ion channels operatively linked to the appropriate promoter so that they are rendered sensitive to the exogenously applied stimulus. These muscle cells are then strengthened through a regimen of stimulation.

In yet another example of a therapeutic approach utilizing the present invention, there is provided a method of treating Parkinson's disease. This method comprises sensitizing those neuronal cells implicated in muscle tremors, so that they are rendered sensitive to activation or deactivation by the exogenously applied stimulus. The firing of these neuronal cells is then controlled through a regimen of stimulation (Birder, Nakamura et al. 2002; Carbon and Eidelberg 2002).

In each of the applications described above, cell activation is achieved by contacting a cell expressing the heterologous stimulus-gated ion channel with an appropriate ligand, or in some circumstances where local effects can be achieved through the application of physical stimuli such as light or temperature. This contacting can occur through systemic introduction of ligand, although this limits the ability to achieve fine control of the time course of the activation; or through localized delivery of ligand. Localized delivery of the ligand can be achieved in several ways. For unmodified ligand, localized injection or introduction from an implant can be used to provide a measure of temporal control. Preferably, however, the ligand is provided in an inactive form, wherein an activating signal can be provided at the time and location of choice. Photoactivatable caged ligands are particularly suited for this purpose, as are pro-drug formulations of the ligands that can be administered orally or parenterally.

Photoactivatable caged ligands provide for release of the ligand in response to light as a secondary stimulus. Specific example of caged ligands include without limitation DMNB-derivatives such as DMNB-capsaicin, DMNB-menthol and ligand derivatives with other chromophores such as methoxy-nitroindolino derivatives which have large two-photon cross-sections. A synthetic route to these caged species is shown in the Examples below. A caged photolabile ATP, the $P^3$-(1-(4, 5-dimethoxy-2-nitrophenyl-ethyl)(DMNPE) ester of ATP (Kaplan, Forbush et al. 1978; Ding and Sachs 2000) is available commercially from Molecular Probes and can be used experimentally without further purification.

In comparison to the so-called chARGe system described by the present inventors in Zemelman et al. (Zemelman, Lee et al. 2002), the present invention provides numerous beneficial characteristics for sensitization of cells, particularly defined populations of cells. First, expression of a single heterologous gene (as opposed to three genes in the case of chARGe, for example) is sufficient to sensitize a cell to stimulation. The dependence on only one transgene eliminates the need to balance relative expression levels and, as the complexity of genetic manipulations rises sharply with the number of genes involved, simplifies the creation of genetically modified cells, tissues, and organisms.

Figure 2:
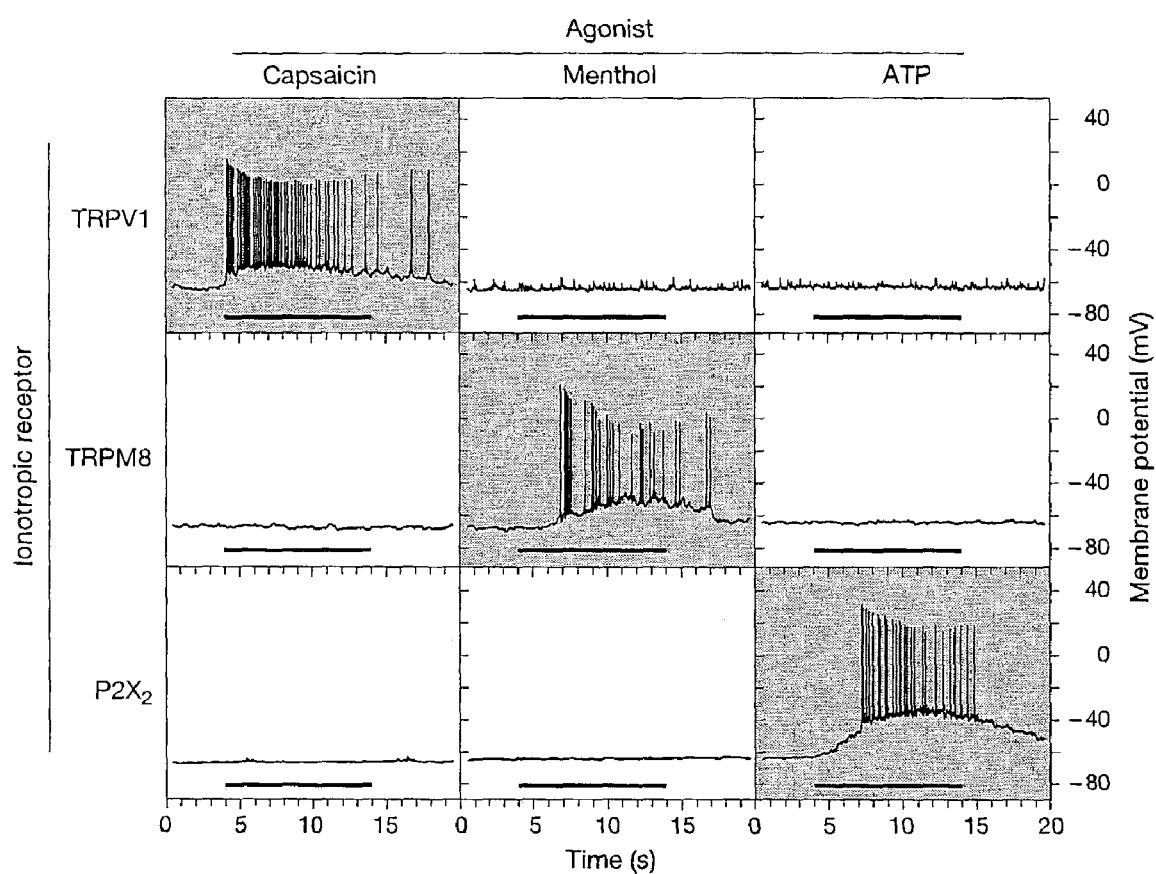
FIG. 2 shows pharmacological stimulation of genetically designated target neurons.

Second, it has been demonstrated that the "on" and "off" kinetics of the cellular response are tightly and reproducibly coupled to those of the stimulus (See examples and FIGS. 2 and 4). This can be further enhanced by controlling the optical stimulus, for example using high-intensity flash photolysis (Rapp 1998) of DMNB-capsaicin or DMNPE-ATP to afford millisecond control over spike times.

Third, the intensity of the response—quantified experimentally in neuronal cells in the examples below as the amount of depolarizing current injected or the firing rate attained—can be graded by varying the concentration of agonist. Although the dose of photons incident on a chARGed neuron can control the intensity of the electrical response, the dose-response relationship is rather loose: firing patterns and firing frequencies of chARGed neurons at identical illumination intensities vary widely (Zemelman, Lee et al. 2002).

Fourth, the three receptor-ligand pairs used in the examples provide distinct sensitization, free from cross talk. (FIG. 2) These receptor-ligand pairs, taken alone or in combination with secondary selection components such as Cre-lox systems and with additional natural or engineered receptor-ligand combinations that will undoubtedly become available in the future, allow multiple distinct populations of neurons to be addressed simultaneously and independently.

Fifth, multiple trigger modes are available to gate the heterologously expressed channels. Agonist can be supplied pharmacologically or optically; TRPV1 and TRPM8 may in addition be controlled by temperature shifts (Caterina, Schumacher et al. 1997; McKemy, Neuhausser et al. 2002; Peier, Moqrich et al. 2002). While the speed, added spatial resolution, and "action at a distance" of photolytic uncaging will make light the trigger of choice for most experiments in vitro and many applications in vivo, there are situations where it may be impractical or unnecessary to direct a light beam or an optical waveguide to a target region. In these circumstances—in behaving animals, or if exquisite temporal control over the response is not essential—pharmacological stimulation offers a powerful alternative. Capsaicin acting on TRPV1 expressed ectopically in nociceptor neurons of *C. elegans*, for example, has elicited "synthetic" avoidance behaviors that wild-type animals lack (Tobin, Madsen et al. 2002). Because agonist will be effective throughout its pharmacological distribution volume, its anatomical sites of action need not be known in advance. This opens the possibility of genetic shotgun searches for the cellular substrates of behaviors: groups of neurons in their normal operational context could be genetically sensitized to stimulation and implicated as carriers of behaviorally relevant information if their activation generates characteristic phenotypes.

The invention will now be further described with reference to the following non-limiting examples.

EXAMPLE 1

Three plasmid species were prepared, each species containing a stimulus-gated ion channel (rat TRPV1, rat TRPM8 or rat $P2X_2$) under the control of the CMV promoter in pCI-fluor, a derivative of the mammalian expression vector pCI-neo (Promega). To create pCI-fluor, the aminoglycoside phosphotransferase coding sequence of pCI-neo was replaced with that of EGFP bearing a 20-amino acid N-terminal GAP43 tag (Zemelman, Lee et al. 2002). Rat TRPV1 and rat TRPM8 were expressed as monomers; rat $P2X_2$ subunits were linked into covalent trimers via tandem repeats of the tripeptide -Ser-Gly-Gly-.

EXAMPLE 2

Hippocampal neurons, obtained from E19 rats and grown in dissociated cultures, were exposed to 4.2 µg cm$^{-2}$ of calcium phosphate-precipitated plasmid DNA as described in Example 1 (pH 7.08) for 20 min to allow plasmid uptake. Transfections were performed on day 8 after plating; immunocytochemical analyses and electrophysiological recordings on days 6-10 after transfection. Lentiviral injections to infect neurons in the mouse brain are described below.

Transfected neurons in cultures and infected neurons in brain slices were identified by GAP43-EGFP fluorescence and recorded in the whole-cell patch-clamp configuration. Patch pipettes (~2.5 megaohms) contained 120 mM K-gluconate, 10 mM KCl, 5 mM ATP, 0.3 mM GTP, and 10 mM K-HEPES (pH 7.2). The extracellular recording solution consisted of 119 mM NaCl, 2.5 mM KCl, 2 mM CaCl2, 1 mM MgCl2, 30 mM glucose, 25 mM Na-HEPES (pH 7.4), 50 µM D,L-2-amino-5-phosphonovaleric acid (AP-5), and 10 µM 6-cyano-7-nitroquinoxaline-2,3-dione (CNQX). Membrane potentials and transmembrane currents were recorded with an Axoclamp-2B amplifier (Axon Instruments) in bridge and continuous single-electrode voltage-clamp mode, respectively, and digitized at 5 kHz without filtering (Digidata 1200, Axon Instruments). Baseline currents were adjusted after break-in to set the membrane potential to −65 mV in current-clamp recordings; voltage-clamp recordings were performed at a holding potential of −65 mV.

The subcellular distribution of one exogenous channel protein, TRPV1, was examined morphologically in cultured neurons. TRPV1 decorated the neuronal plasma membrane in its entirety; it was detected on dendrites, somata, and axons. This distribution suggested that agonist-induced currents could, at least in part, mimic excitatory synaptic input at dendrites and somata. In addition, opening of TRPV1 channels in spike initiation zones (such as the initial axon segment) would be expected to short circuit the neuron's spike generator directly.

EXAMPLE 3

Cultured neurons were fixed in 4% paraformaldehyde, permeabilized in 0.1% Triton X-100, exposed to a blocking solution containing 5% bovine serum and 0.2% gelatin, and stained with rabbit polyclonal affinity-purified antibodies against GFP (1:250) and guinea pig polyclonal antibodies against TRPV1 (1:1,000; Chemicon). Bound antibodies were detected with AlexaFluor-488 and AlexaFluor-594 conjugates (1:500; Molecular Probes), and visualized by wide-field epifluorescence microscopy.

EXAMPLE 4

To prepare photo-releasable caged agonists, Capsaicin (Fluka) was reacted with 4,5-dimethoxy-2-nitrobenzyl chloroformate (Aldrich) according to the reaction scheme in FIG. 1. To a solution of capsaicin (10.7 mg, 0.035 mmol) in methylene chloride (CH2Cl2; 2 ml) at 0° C. were added ~5 equivalents of 4,5-dimethoxy-2-nitrobenzyl chloroformate (46.9 mg, 0.170 mmol), followed by ~2 equivalents of triethylamine (10 µl, 0.072 mmol). The reaction mixture was stirred in the dark for 2 hours at room temperature, sufficient to allow quantitative conversion of capsaicin to the caged product. The reaction was monitored by thin layer chromatography on silica gel, using 50% ethyl acetate/hexanes as the mobile phase. DMNB-capsaicin migrates at an Rf of 0.10 in this system. The reaction mixture was concentrated to ~100 µl in the dark under a stream of argon, diluted with 1 ml 50% ethyl acetate/hexanes, and chromatographed on a silica gel column (E. Merck, 230-400 mesh). The column was developed with a gradient of 50-70% ethyl acetate/hexanes, and fractions at Rf 0.10 were combined and concentrated on a rotary evaporator to yield DMNB-capsaicin quantitatively (18.9 mg, 99%). The compound was dissolved at 100 mM in anhydrous dimethyl sulfoxide (DMSO) and stored at −80° C. under argon. For photostimulation experiments, a working stock of 5 mM DMNB-capsaicin in DMSO was freshly diluted to 5 µM in extracellular recording solution. DMNB-capsaicin was characterized by 1H NMR and mass spectrometry with results consistent with those anticipated for the structure.

EXAMPLE 5

To evaluate the ability to provide pharmacological stimulation to cells expressing heterologous stimulus-gated ion channels, a 1-ml bolus of agonist was perfused into an RC-26G recording chamber (Warner Instruments) containing transfected cells or virus-infected brain slice at a laminar flow rate of ~6 ml min$^{-1}$.

Irrespective of the type of heterologous channel present, the membrane potentials of the neurons, recorded under whole-cell current clamp in the presence of glutamate receptor antagonists (50 µM AP-5 plus 10 µM CNQX), remained stably at resting levels in the absence of ligand.

The resting potentials of transfected neurons (−50.6±9.6 mV; mean±s.d., n=30) tended to be more positive than those of untransfected cells (−59.7±2.9 mV; mean±s.d., n=4), suggesting that the presence of the heterologous channels created small depolarizing leakage currents. The application of a bolus of agonist (50 nM capsaicin, 100 µM menthol, 50 µM ATP) led to a characteristic sequence of depolarization, spiking, and repolarization (FIG. 2) whose time course reflected the "pharmacokinetics" of agonist delivery—the dead volume of the perfusion apparatus, the volume of the agonist-containing bolus, and the exchange time of the recording chamber. The pharmacological specificity of stimulation was absolute: of the nine possible receptor-agonist combinations tested, only the three cognate matches, depicted in the diagonal of FIG. 2, elicited responses. None of the three agonists, including ATP, was able to stimulate hippocampal neurons lacking the cognate exogenous receptor (see the off-diagonal entries in FIG. 2): as intended, responsiveness to the broadly applied pharmacological stimulus was restricted to a genetically delimited population of targets.

Figure 3A:
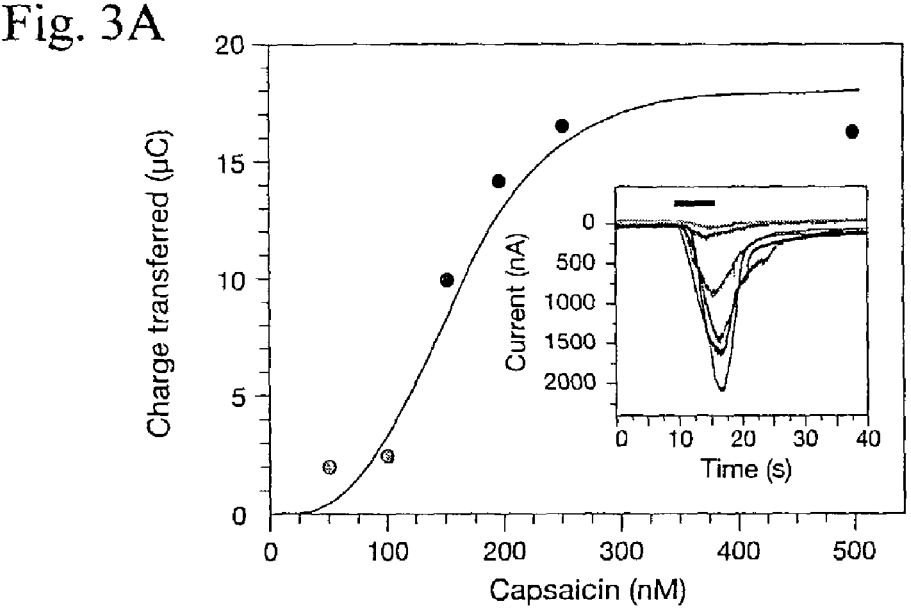
FIGS. 3A and B show dose dependence of the capsaicin response in TRPV1-expressing neurons.
Figure 3B:
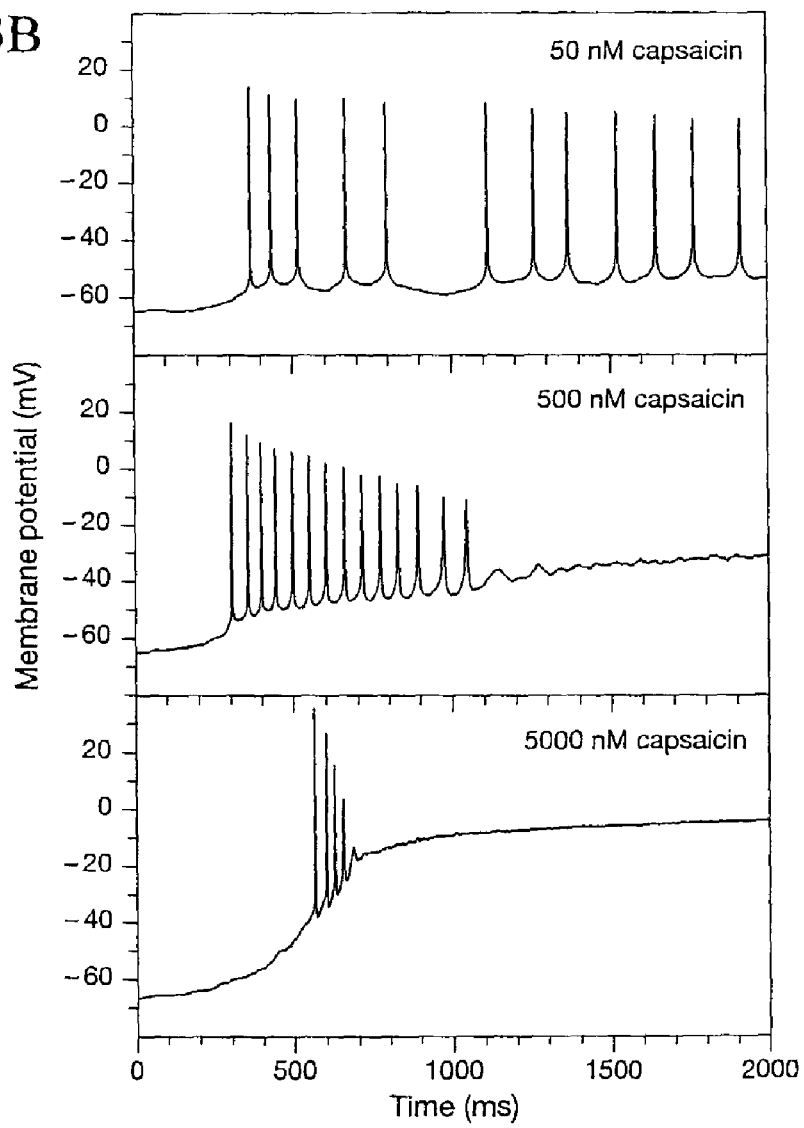

To determine dose-response relationships, the peak amplitudes as well as the integrated charges carried by depolarizing currents at different agonist concentrations were measured under whole-cell voltage clamp, at a constant holding potential of −65 mV. As illustrated for TRPV1 in FIG. 3A, current amplitudes and charge transfers saturated: half-maximal responses were seen at ~150 nM capsaicin; the pseudolinear response range extended from 70 to 200 nM. TRPM8 showed a qualitatively similar dose-response curve, with a half-maximal response at 150 µM menthol (results not shown). The maximal agonist-induced currents varied considerably from neuron to neuron (range: 360-2457 nA, n=8), presumably as a result of differences in neuronal surface areas and channel densities due to variable copy numbers of transfected plasmid. Under the assumptions of a 35-pS single-channel conductance at −65 mV (Caterina, Schumacher et al. 1997) and linear summation of current, we estimate that transfected neurons expressed between 160,000 and 1,000,000 functional TRPV1 channels. Because the amount of depolarizing current injected into a neuron could be controlled by titrating the concentration of agonist (FIG. 3A), the frequency of action potentials should be tunable as well. Current-clamp recordings displayed in FIG. 3B demonstrate that this was indeed the case. Spike rates, evaluated in sliding 200-ms windows, rose as a function of increasing concentration of agonist, peaking at a frequency of 40 Hz in our data set (382 agonist applications to 60 neurons). In contrast to the simple sigmoidal dose-response relationship that characterized peak and integrated channel currents (FIG. 3A), the relationship between agonist concentration and firing frequency was complicated by nonlinearities intrinsic to the mechanism of spike generation. Departures from sigmoidal behavior were particularly evident at elevated agonist concentrations (FIG. 3B, 500 and 5,000 nM capsaicin). Rapid depolarization rates led to a brief burst of spikes at high frequency that was followed by a long-lasting plateau during which the membrane remained depolarized but action potentials were absent (FIG. 3B, bottom). In all likelihood, the lack of excitability during the plateau phase reflects the accumulation of voltage-gated sodium channels in the inactivated state, in which they remain trapped until the membrane is repolarized. Intermittent delivery of agonist may help to remove inactivation and sustain high firing rates over extended periods of time.

EXAMPLE 6

A particularly attractive way of delivering pulses of agonist is to photorelease the active compound from an inactive, photolabile precursor (Kaplan, Forbush et al. 1978; Walker, McCray et al. 1986; McCray and Trentham 1989; Wilcox, Viola et al. 1990; Callaway and Katz 1993). One such precursor, the P3-(1-(4,5-dimethoxy-2-nitrophenyl)ethyl) (DM-NPE) ester of ATP (Kaplan, Forbush et al. 1978; Ding and Sachs 2000), was available from a commercial source (Molecular Probes); another was synthesized by reacting capsaicin with 4,5-dimethoxy-2-nitrobenzyl (DMNB) chloroformate to attach a DMNB blocking group in carbonate ester linkage to the phenolic hydroxyl function of capsaicin (FIG. 1 and Example 3), a molecular feature important for agonist activity (Walpole, Wrigglesworth et al. 1993; Walpole, Bevan et al. 1996). Absorption of photons in the near-UV wavelength range (absorption maximum ~355 nm) by the DMNB and DMNPE chromophores is expected to produce reactive aci-nitro intermediates, which, in a series of rate-limiting dark reactions, liberate the free agonists (McCray and Trentham 1989).

The presence of the DMNB or DMNPE blocking groups rendered capsaicin and ATP biologically inert, presumably by sterically preventing the caged ligands from binding to their respective receptors. The membrane potentials and transmembrane conductances of neurons expressing TRPV1 or P2X$_2$, recorded in whole-cell current- or voltage-clamp mode, respectively, were unaffected by the presence of 5 µM DMNB-capsaicin and 1 mM DMNPE-ATP, concentrations that exceeded the saturating levels of the free agonists, determined in FIG. 3A, 10- to 20-fold. No trace of biological activity due to chemical or enzymatic decomposition of the caged compounds was detected in recordings lasting for>30 min.

Figures 4A, 4B:
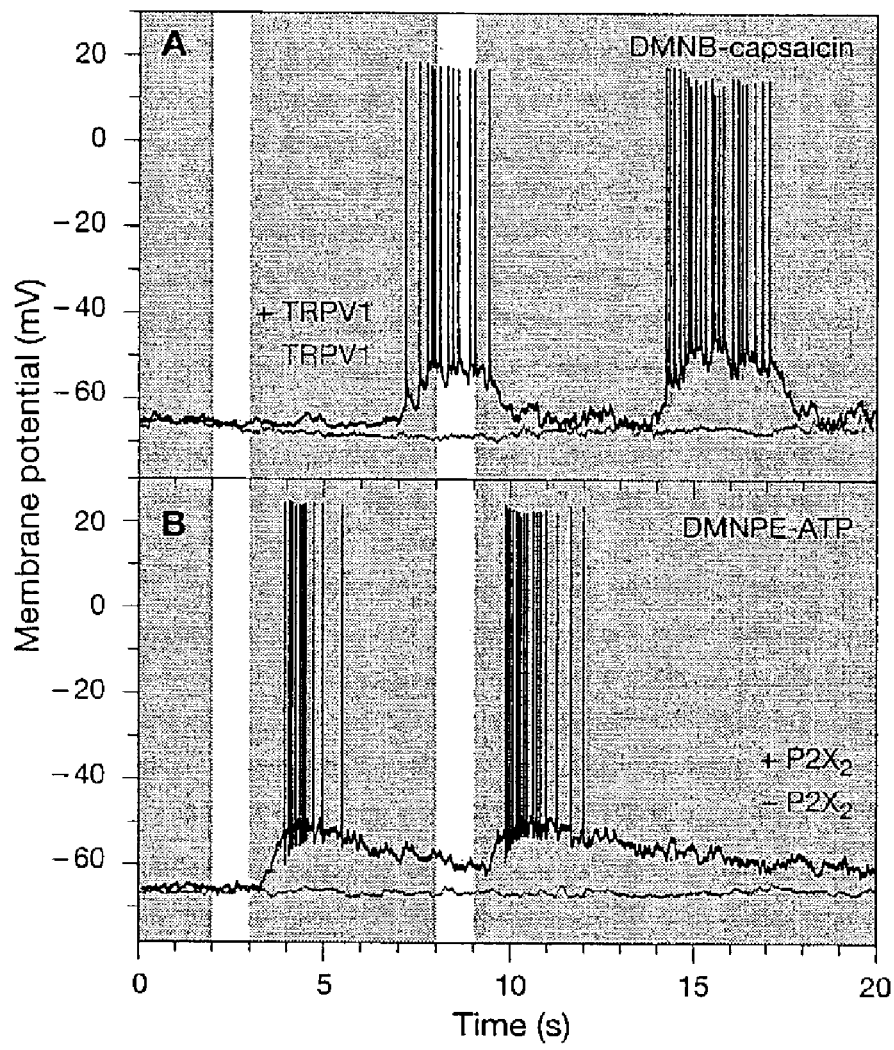
FIGS. 4A and B show photostimulation of genetically designated target neurons, in which the membrane potentials of hippocampal neurons expressing TRPV1 (A, black trace) or P2X$_2$ (B, black trace), or of untransfected control neurons, (A and B, grey traces) are shown.

Whole-field illumination with the collimated, unfiltered output of a mercury arc lamp delivered 26 mW mm$^{-2}$ of optical power at wavelengths<400 nm. In the presence of 5 µM DMNB-capsaicin, TRPV1-positive neurons within the illuminated field—but not untransfected neurons—responded to the optical stimulus with a flurry of activity (FIG. 4A). Following a single light pulse lasting for 1 s, action potentials were fired at frequencies of 15-40 Hz. Activity was confined to a sharply delimited window in time whose onset lagged behind that of the optical stimulus by a predictable interval (5,035±2,061 ms; mean±s.d., n=10), and whose duration (2,651±383 ms; mean±s.d., n=10) slightly exceeded that of the light exposure. Repeated photostimulation of the same neuron was followed by stereotyped responses that did not attenuate (FIG. 4A).

P2X$_2$-positive neurons exposed to a 1-s light pulse in the presence of 1 mM DMNPE-ATP exhibited light-evoked responses that were qualitatively similar to those of TRPV1-positive neurons in the presence of DMNB-capsaicin but showed distinctive temporal characteristics (FIG. 4B). The window of activity followed the optical stimulus after a shorter lag period (1,136±96 ms; mean±s.d., n=16), lasted for a slightly shorter span of time (2,456±1,273 ms; mean±s.d., n=16), and returned to baseline more gradually than the TRPV1 response. Different uncaging and channel gating kinetics are likely to underlie these characteristic temporal response patterns. The mechanistic basis of the observed response latencies is currently unknown, but comparatively low illumination intensities may play a role. The light pulses used in our experiments carried an optical energy of 26 mJ mm$^{-2}$ in the spectral band<400 nm during a 1-s exposure; high-intensity flash lamps or UV lasers compress comparable energies into a few hundred microseconds (Callaway and Katz 1993; Rapp 1998) and may thus elicit instant, precisely timed responses.

To photostimulate in vivo, the sensitized target cells are illuminated by the ultraviolet (wavelength: 355 nm) output of a continuous-wave diode laser through a multimode optical fiber. Low energy laser pulses launched into the fiber produce an abrupt concentration jump from the caged to the active ligand in a small volume of tissue.

EXAMPLE 7

To generate the lentivirus vectors for transgenesis and transient ion channel expression the double stranded cloning cassette GGATCCCGTACGATAACTTCGTATAG-CATACATTATACGAAGTTATCGTACGGGCGC GCCCG-GACCGGAATTC (Seq ID No: 4) was digested with BamH1 and EcoR1 and inserted into the same restriction sites in an existing lentiviral backbone pFUGW, consisting of 5' and 3'LTRs, the ubiquitin promoter, the flap, and the WRE sequences (Lois, Hong et al. 2002). GAP43-EGFP sequence (Zemelman, Lee et al. 2002) and DsRed2 sequence (Clontech) were amplified and fused to ECMV IRES sequence (Clontech) using PCR. EcoR1 and Pac1 restriction sites were introduced at the 5' and 3' ends, respectively, using PCR primers. Ion channel cDNAs were also amplified using PCR, and Asc1 restriction sites were added at both ends of the genes. The construction of the P2X$_2$ covalent trimer has been described previously (Zemelman, Nesnas et al. 2003). The fluorescent protein genes were inserted into the EcoR1-Pac1 sites in the lentiviral cloning cassette. Each ion channel gene was then inserted into the Asc1 site to generate the transient expression lentivirus vectors (FIG. 5A-D).

To generate the lentivirus vectors for transgenesis, 5' loxP cloning cassette AAGCTTCGTACGATAACTTCGTATAG-CATACATTATACGAAGTTATAGAAACAGGGA TCCTCTAGAGCCACCATGG (Seq. ID No: 5) was inserted into the HindIII-Nco1 restriction sites in the pEGFP vector (Clontech). The 3' loxP cloning cassette GCGGC-CGCTAATTAGTTGAATAACTTCGTATAG-CATACATTATACGAAGTTATCGTA CGGAATTC (Seq. ID No. 6) containing the translation termination codons in each of the three reading frames was inserted Not1-EcoR1 into the same vector. The resulting construct was digested with BsiW1 and inserted into the same restriction site in the lentivirus vector, introducing a loxP-stop-loxP cassette between the promoter and the ion channel genes (FIG. 6A).

To replace the ubiquitin promoter with the β-actin promoter (Miyazaki, Takaki et al. 1989), the latter was amplified using PCR to generate Pac1 and Spe1 sites at the 5' and 3' end of the promoter, respectively. The ubiquitin promoter was removed with the same restriction enzymes. Promoter replacement preceded the insertion of other sequences into the lentivirus vector backbone (FIG. 6B).

In some cases the IRES and the trailing fluorescent protein gene were not incorporated into the lentivirus vector (FIG. 6C, D).

Concentrated stocks of infectious viral particles, are prepared as previously described (Naldini, Blomer et al. 1996; Zufferey, Nagy et al. 1997). Briefly, 293T cells are simultaneously transfected with three plasmids: one of the plasmids derived from pFUGW containing the stimulus-gated ion channel gene (see FIG. 6), the packaging plasmid pCM-VdeltaR8.2 (Naldini, Blomer et al. 1996), and a plasmid encoding an envelope glycoprotein. Examples of envelope glycoproteins include those of viruses such as vesicular stomatitis virus (VSV) (Naldini, Blomer et al. 1996), Ebola virus (Wool-Lewis and Bates 1998), Mokola virus (Mochizuki, Schwartz et al. 1998), lymphocytic choriomeningitis virus (LCMV) (Beyer, Westphal et al. 2002), murine leukemia virus (MuLV) (Kobinger, Weiner et al. 2001), Ross River virus (RRV) (Kang, Stein et al. 2002). The transfection is carried out using Fugene (Roche). Cell supernatant is collected 48-60 hours post transfection, filtered using a 0.45 μm low protein binding membrane (Nalgene), and spun 90 min at 25,000 rpm to pellet the viral particles. Titers will be determined by serial dilution on HeLa cells, followed by detection of the expression of the heterologous stimulus-gated ion channel or a fluorescent marker protein by immunofluorescence microscopy.

EXAMPLE 8

The genomic targeting constructs were created using the genomic ion channel genes. To find the genomic region containing TRPV1 rat genomic BAC library RPCI23 (BACPAC Resource Center, Children's Hospital Oakland Research Institute, Oakland, Calif.) was screened with a DNA probe

```
                                            (Seq. ID No: 7)
ATGGAGCAACGGGCTAGCTTAGACTCAGAGGAGTCTGAGTCCCCACCCCA

AGAGAACTCCTGCCTGGACCCTCCAGACAGAGACCCTAACTGCAAGCCAC

CTCCAGTCAAGCCCCACATCTTCACTACCAGGAGTCGTACCCGGCTTTTT

GGGAAGGGTGACTCGGAGGAGGCCTCTCCCCTGGACTGCCCTTATGAGGA

AGGCGGGCTGGCTTCCTGCCCTATCATCACTGTCAGCTCTGTTCTAACTA

TCCAGAGGCCTGGGGATGGACCTGCCAGTGTCA
``` representing the first exon of the gene. The BAC clone identified in the screen was digested with BsiW1 and subjected to Southern blotting using the same probe to ensure that it contained the required genomic region. To reduce the size of the final genomic targeting vector, a hybrid genomic-cDNA TRPV1 gene was constructed using the SacII restriction site in exon 7 of the gene. As a result, the hybrid TRPV1 gene was genomic up to exon 7 and cDNA from exon 7 until the stop codon. Using PCR, the hybrid TRPV1 was fused to ECMV IRES and fluorescent protein cDNA. At the same time, Sal1 and Not1 sites were added to the 5' and 3' ends of the resulting DNA molecule, respectively. This DNA fragment was inserted into the Sal1-Not1 sites in transfer plasmid pBigT (Srinivas, Watanabe et al. 2001). The resulting vector was digested with Pac1 and Asc1 restriction enzymes and inserted into the pROSA26PA genomic targeting vector (Srinivas, Watanabe et al. 2001). While the ROSA26 genomic region contains an endogenous promoter sufficient for ubiquitous expression of the incorporated genes, for some constructs an additional CAG promoter (Miyazaki, Takaki et al. 1989) was amplified using PCR, creating Pac1 restriction sites at both ends of the sequence, and inserted into the Pac1 site in pROSA26PA. The resulting vectors (FIG. 7A) were used to generate ES cells with the stably integrated ion channel gene followed by the IRES and fluorescent protein sequence using G418 selection (Hogan, Beddington et al. 1994; Ausubel, Brent et al. 2003). To ensure that only homologous recombinants were selected, the vector contained a diphtheria toxin gene (DTA), which is lost following homologous genomic integration of the vector (Soriano 1999). Resulting ES cells were processed as described elsewhere (Ausubel, Brent et al. 2003).

To identify the genomic region containing the $P2X_2$ gene rat genomic BAC library RPCI23 was screened with a DNA probe (Seq ID No: 8)
GGTGAAGGACCAACTTTGGGAGAAGGGGCAGAGCTACCACTGGCTGTCCA

GTCTCCTCGGCCTTGCTCCATCTCTGCTCTGACTGAGCAGGTGGTGGACA

CACTTGGCCAGCATATGGGACAAAGACCTCCTGTCCCTGAGCCTTCCCAA

CAGGACTCCACATCCACGGACCCCAAAGGTTTGGCCCAACTTTGA representing the last exon of the gene. The BAC clone found in the screen was digested with Apa1 restriction enzyme and subjected to Southern blotting using the same probe to ensure that it contained the required genomic region. Genomic $P2X_2$ was amplified using PCR and fused to ECMV IRES and fluorescent protein, creating Sal1 and Not1 sites at the 5' and 3' end of the molecule, respectively, as described for TRPV1 above. However, and additional Xho1 restriction site was also introduced during PCR immediately 5' of $P2X_2$ stop codon. The amplified DNA fragment containing $P2X_2$, IRES and the fluorescent protein was inserted into the Sal1-Not1 sites in transfer plasmid pBigT (Srinivas, Watanabe et al. 2001). The resulting vector was digested with Pac1 and Asc1 restriction enzymes and inserted into the pROSA26PA genomic targeting vector (Srinivas, Watanabe et al. 2001). For some constructs an additional CAG promoter (Miyazaki, Takaki et al. 1989) was amplified using PCR, creating Pac1 restriction sites at both ends of the sequence, and inserted into the Pac1 site in pROSA26PA. The $P2X_2$ genomic targeting vectors (FIG. 7B) were used to generate ES cells with the stably integrated ion channel gene followed by the IRES and fluorescent protein sequence using G418 selection (Hogan, Beddington et al. 1994; Ausubel, Brent et al. 2003). To ensure that only homologous recombinants were selected, the vector contained a diphtheria toxin gene (DTA), which is lost following homologous genomic integration of the vector (Soriano 1999). Resulting ES cells were processed as described elsewhere (Ausubel, Brent et al. 2003).

To generate trimeric genomic $P2X_2$ (FIG. 7C), pBluescriptII (Stratagene) was digested with BamH1, the site filled in with T4 DNA polymerase, and the vector re-circularized. The vector was then digested with Xho1 and a cloning cassette inserted containing a BamH1 restriction site. The second and third subunits of the trimeric cDNA $P2X_2$ (Zemelman, Nesnas et al. 2003) were excised with BamH1 and inserted into this vector. The two subunits were then removed with Xho1 and inserted into the Xho1 cloning site of the pBigT (Srinivas, Watanabe et al. 2001) transfer vector containing the genomic $P2X_2$, IRES and the fluorescent protein sequences. The resulting construct was digested with Pac1 and Asc1 restriction enzymes and inserted into the pROSA26PA genomic targeting vector (Srinivas, Watanabe et al. 2001) and processed as described above.

EXAMPLE 9

The most commonly used chromophores for single-photon uncaging are nitrobenzyl derivatives such as 4,5-dimethoxy-2-nitrobenzyl (DMNB) or P3-(1-(4,5-dimethoxy-2-nitrophenyl)ethyl) (DMNPE) groups, which can be attached to virtually any chemical functionality (carboxylate, amine, phenol, hydroxyl, sulfhydryl, carbamate, amide, phosphate, etc. (Walker, McCray et al. 1986; Walker, Reid et al. 1989). Absorption by these chromophores of photons in the near-UV wavelength range (peak ~355 nm) creates reactive aci-nitro intermediates, which, in a series of rate-limiting dark reactions, release the active agonists (McCray and Trentham 1989).

The uncaged precursors, (−)-menthol ([1R,2S,5R]-5-methyl-2-[1-methylethyl]cyclo-hexanol; Sigma) and icilin (1-[2-hydroxyphenyl]-4-[3-nitrophenyl]-1,2,3,6-tetrahydropyrimidine-2-one; Phoenix Pharmaceuticals), are available commercially. Both molecules contain hydroxyl groups that may be derivatized with 4,5-dimethoxy-2-nitrobenzyl chloroformate (Aldrich) in a reaction scheme identical to that used in our earlier synthesis of DMNB-capsaicin (Zemelman, Nesnas et al. 2003). Products are purified on silica gel, using 5% methanol/methylene chloride for caged icilin and 10% ethyl acetate/hexanes for caged menthol. The purified compounds are concentrated on a rotary evaporator, and stored at −80° C. under argon. All procedures are performed under safelight conditions; DMNB derivatives are characterized by 1H NMR (Bruker 500 MHz) and mass spectrometry (JEOL LCmate). The abilities of the caging groups to block biological activity, as well as the physical parameters of photolytic uncaging, are assayed as follows.

Figure 8:
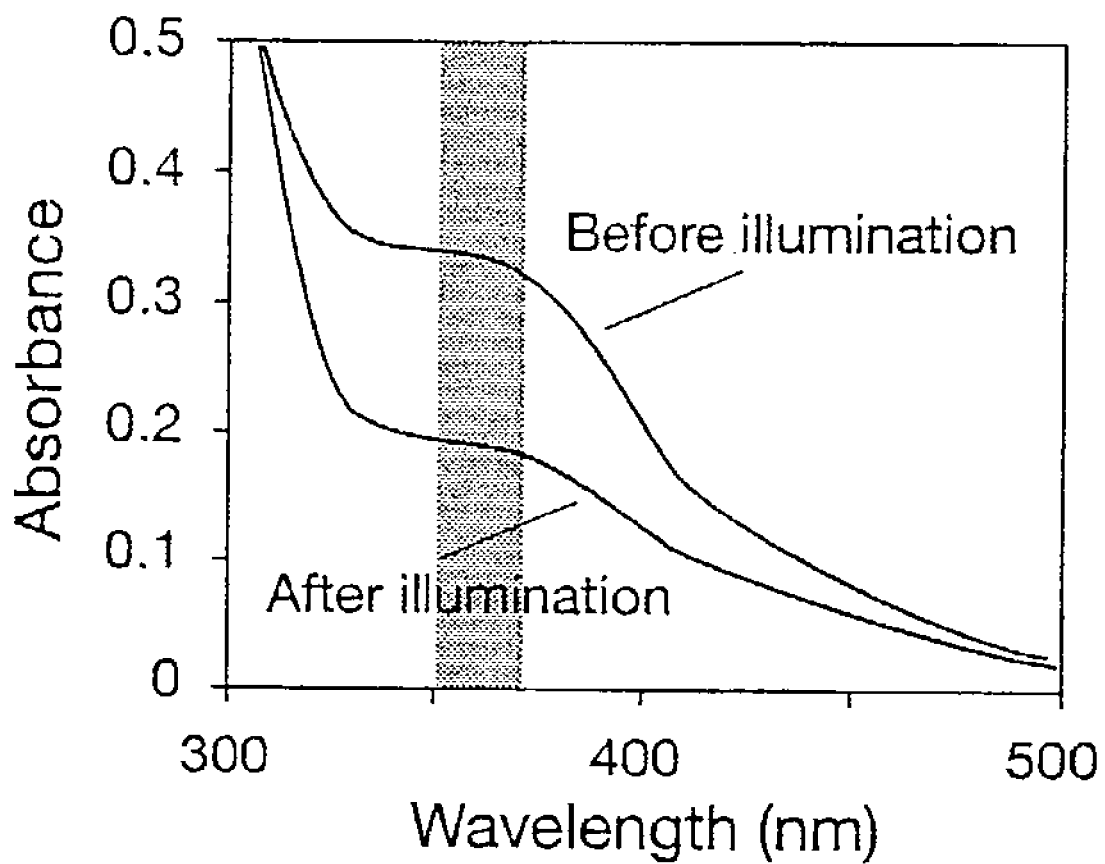
FIG. 8 shows spectroscopic measurement of photolytic uncaging. Exposure of a example of 5 μM DMNB-capsaicin in extracellular recording solution supplemented with 100 nM DTT to 0.371 mJ of optical energy at wavelengths<400 nm leads to 44% photolysis. The reaction of DMNB-capsaicin photolyzed is quantified as the reduction in absorbance in the 350-370 nm wavelength band (shaded area).

To monitor the uncaging reaction, we have adapted a simple spectroscopic assay (Walker, Reid et al. 1989; Marriott 1994) that records the reduction in the intensity of the ~360-nm absorption band following photolysis of the 4,5-dimethoxy-(2-nitrophenyl)-ethyl or 4,5-dimethoxy-(2-nitrobenzyl) caging groups to the respective nitroso photoproducts, 4,5-dimethoxy-(2-nitrosoacetophenone) and 4,5-dimethoxy-(2-nitrosobenzaldehyde), and their adducts with DTT (FIG. 8). The assay is used, in conjunction with a monochromator (Jovin-SPEX) and an optical power meter (Newport 1930-C), to measure action spectra and energy requirements of uncaging for all of our caged agonists.

EXAMPLE 10

Brain slices are obtained from mice at P15 to P20. Mice are anesthetized with an intraperitoneal injection of a mixture of 120 mg/kg ketamine (Sigma) and 10 mg/kg xylazine (Sigma) in saline. When the animals do no longer respond to pain (toe pinch), they are decapitated with scissors. The skull is exposed through a midline incision with a scalpel. Using medium-size scissors, the skull is carefully cut in the midline and the two flaps folded sideways, baring the cortex. After cranial nerves and brain stem are gently severed with a bent spatula, the brain is transferred to a beaker filled with ice-cold bicarbonate-ACSF that is bubbled with 95% $O_2$ and 5% $CO_2$; the solution contains 124 mM NaCl, 3 mM KCl, 1 mM $CaCl_2$, 3 mM $MgSO_4$, 1.25 mM $NaH_2PO_4$, 26 mM $NaHCO_3$, and 10 mM glucose. The brain is allowed to cool for at least 2 minutes and then trimmed with a razor blade. Two coronal cuts remove cerebellum and frontal lobe; one horizontal cut removes ventral structures, including midbrain and most of the diencephalon.

To mount the trimmed brain for slicing, an agar cube (5% in ACSF) is glued to the metal base of the vibratome. The tissue block is then set in place in a vertical orientation (frontal surface pointing up) and the posterior (occipital) plane glued to the metal base with cyanoacrylate (Superglue). The ventral (horizontal) plane faces the agar block. The chamber is flooded with ice-cold ACSF, and the brain is sliced into 300-μm thick coronal slices using a vibratome (Carl Zeiss). Individual slices are gently removed with the blunt end of a Pasteur pipette and deposited in the incubation chamber, which consists of a supported nylon netting inside a plastic beaker filled with bicarbonate-ACSF that is bubbled with 95% $O_2$ and 5% $CO_2$ and kept at room temperature. Experiments are performed within 1-11 hours after slicing.

EXAMPLE 11

To apply a temperature stimulus to the cultured neurons or explanted neural tissue, extracellular recording solution (see above) used to perfuse the recoding chamber was directed through a custom-made Peltier heating/cooling element connected to a temperature controller (Melcor; Alpha Omega Series 800 controller) and feedback-regulated by an inline thermoelectric element (CSC32, Omega). The activity of neurons in cultures or explanted tissues superfused with thermostatted (i.e., heated or cooled) recording solution was monitored electrically, as described above.

To apply a temperature stimulus in vivo, the sensitized target cells are contacted with a thermal signal generator probe that is capable of producing arbitrarily shaped bipolar (heating or cooling) thermal swings in a small volume of tissue. Heating or cooling of the probe is achieved by means of a Peltier thermoelectric device. The probe temperature measured directly at the site of contact by a thermoelectric element is controlled using closed-loop circuitry. Alternatively, the sensitized target cells are illuminated by the infrared (wavelength range: 808-1064 nm) output of a continuous-wave diode laser through a multimode optical fiber. Low energy laser pulses launched into the fiber produce an abrupt temperature rise in a small volume of tissue that can be measured directly at the site of illumination by a thermoelectric element.

EXAMPLE 12

To induce transient ion channel expression in specific regions of the mouse brain using lentivirus vectors, the following protocol is used. Mice are anesthetized with ketamine-xylazine (ketamine, 100 mg/kg; kylazine, 10 mg/kg). The dorsal aspect of the head and neck is shaved and prepped in sterile fashion. The animal is kept warm during the procedure. For intraparenchymal or intraventricular injections, a midline incision overlying the skull is carried out to reveal the coronal, sagittal, and lambdoid sutures. The mouse is then placed in a stereotactic apparatus (David Kopf Instruments) maintaining the sutures on a level plane. The bregma is identified and used as zero coordinate. For intraparenchymal injections, a 1-mm burr hole is made at coordinate +2.0 mm lateral and −0.3 mm caudal to the bregma. Other coordinates are derived from the Atlas of the Mouse Brain (second edition, Academic Press). A 26-gauge needle on a 10-ml Hamilton syringe is then stereotactically inserted via the burr hole into the right striatum at a depth of 3 mm from the dura. Five microliters of virus suspended in 20% sucrose (final concentration, $2\times10^9$ IU/ml), is injected with a precision pump over 10 min (0.5 μl/min). The needle is left in place for 5 min and then slowly withdrawn. Bone wax is applied to the burr hole, and the wound is closed with 4-0 nylon suture. The animals are allowed to recover under a heat lamp. 7-10 days after surgery the sutures are removed. Two weeks after the injection the animal is sacrificed, its brain extracted and immediately sliced using a microtome as described in Example 10.

EXAMPLE 13

To make transgenic mice using lentivirus vectors, the following protocol is used. Female mice are superovulated and mated with fertile males to produce embryos. For this, pre-pubescent female mice around 25 days of age and weighing between 12.5 and 14 grams are injected intraperitoneally with 5 IU of PMS (Sigma G 4527, 25 IU/ml in 0.9% NaCl) between 1 and 3 p.m. on day −2, followed by 5 IU of HCG (Sigma C 8554, 25 IU/ml in 0.9% NaCl) 48 hours later on day 0. Hormone treated females are caged with fertile males to mate overnight. On the morning of day 1, females are checked for copulation plugs. Female mice are sacrificed on day 2 and 4-6 cell stage embryos are collected for viral infection.

The zona pellucida of the fertilized oocytes is removed by incubation in acidic Tyrode solution at room temperature. When the zonae appear to be dissolved, embryos are washed in medium and then transferred into 50 μl microdrops of viral suspension under mineral oil in a petri dish. To prevent loss of embryos due to sticking to the glass walls of the transfer pipettes are pre-coated with 1% albumin in PBS or, alternatively, plastic transfer pipettes are used. Between 5 and 10 embryos are cultured individually in separate microdrops to prevent them from adhering to one another. The viral suspension can be diluted to various concentrations to roughly control the average number of proviral integrations expected per transgenic genome. Zygotes are incubated in the viral suspension 12-24 hours and removed by disposable transfer pipet to a dish of media for washing. It is helpful to culture the embryos for 2 days to check for gene expression consistent with the presence of the introduced viral genome, which carries a color marker. After extensive washing in media, infected embryos are transferred to pseudopregnant females.

Based on the foregoing, it will be understood that the present invention provides numerous inventive advances in the art, including without limitation:

(1) chemical compositions comprising novel expression units, each expression unit including a sequence encoding a functional stimulus-gated ion channel; a promoter effective to result in expression of the ion channel in mammalian cells, and cell-type specific control elements that limit the expression of the ion channel except in cells of a specific type or character; and physical or chemical ligands, caged or not, that gate the stimulus-gated ion channel.

(2) a method for investigating the role of a specific cell type in a disease or condition, comprising the steps of (a) obtaining an expression unit including a sequence encoding a functional stimulus-gated ion channel; a promoter effective to result in expression of the ion channel in mammalian cells, and cell-type specific control elements which limit the expression of the ion channel except in cells of the specific cell-type, (b) introducing the expression unit into the cells (preferably in vivo) and expressing the ion channel; (c) triggering the ion channel using a specific stimulus; and (d) observing the effects, if any, of triggering the ion channel.

(3) a method for investigating the role of a specific cell type in alleviating a disease or condition, comprising the steps of (a) obtaining an expression unit including a sequence encoding a functional stimulus-gated ion channel; a promoter effective to result in expression of the ion channel in mammalian cells, and cell-type specific control elements which limit the expression of the ion channel except in cells of the specific cell-type, (b) introducing the expression unit in vivo into the cells of the organism exhibiting a disease or condition and expressing the ion channel; (c) triggering the ion channel using a specific stimulus; and (d) observing the effects, if any, of triggering the ion channel on the exhibited disease or condition.

(4) a method for treating diseases or conditions associated with inappropriate activity of specific cell types. After determining that a specific cell type plays a role in a disease or condition, as in (2) above, heterologous stimulus-gated ion channels are introduced into individuals suffering from the disease or conditions in expression units expressed in the specific cell type. These ion channels are selectively triggered to provide a therapeutic benefit to the individual.

(5) a method for evaluating compositions for use in treating disease or conditions associated with inappropriate activity of specific cell types. After determining that a specific cell type plays a role in a disease or condition, as in (2) above, the cell type can be used in a screening procedure to select other molecules, preferably small molecules suitable for chemical synthesis that result in the same or opposite response as that obtained by triggering the heterologous stimulus-gated ion channel.

(6) genetically-engineered cells and organisms, include non-human mammalian knock-in and transgenic mammals expressing a heterologous stimulus-gated ion channel.

(7) chemical ligands, caged or not, that gate the stimulus gated ion channel.

The following references are cited herein and are each incorporated herein by reference as though fully set forth.

Arnold, D. B. and N. Heintz (1997). "A calcium responsive element that regulates expression of two calcium binding proteins in Purkinje cells." *Proc Natl Acad Sci U S A* 94(16): 8842-7.

Ausubel, F. M., R. Brent, et al., Eds. (2003). *Current Protocols in Molecular Biology*. New York, John Wiley & Sons.

Awatramani, R., P. Soriano, et al. (2001). "An Flp indicator mouse expressing alkaline phosphatase from the ROSA26 locus." *Nat Genet* 29(3): 257-9.

Bainbridge, J. W., C. Stephens, et al. (2001). "In vivo gene transfer to the mouse eye using an HIV-based lentiviral vector; efficient long-term transduction of corneal endothelium and retinal pigment epithelium." *Gene Ther* 8(21): 1665-8.

Bex, A., M. Vooijs, et al. (2002). "Controlling gene expression in the urothelium using transgenic mice with inducible bladder specific Cre-lox recombination." *J Urol* 168(6): 2641-4.

Beyer, W. R., M. Westphal, et al. (2002). "Oncoretrovirus and lentivirus vectors pseudotyped with lymphocytic choriomeningitis virus glycoprotein: generation, concentration, and broad host range." *J Virol* 76(3): 1488-95.

Birder, L. A., Y. Nakamura, et al. (2002). "Altered urinary bladder function in mice lacking the vanilloid receptor TRPV1." *Nat Neurosci* 5(9): 856-60.

Bishop, A., O. Buzko, et al. (2000). "Unnatural ligands for engineered proteins: new tools for chemical genetics." *Annu Rev Biophys Biomol Struct* 29: 577-606.

Brake, A. J. and D. Julius (1996). "Signaling by extracellular nucleotides." *Annu Rev Cell Dev Biol* 12: 519-41.

Brake, A. J., M. J. Wagenbach, et al. (1994). "New structural motif for ligand-gated ion channels defined by an ionotropic ATP receptor." *Nature* 371(6497): 519-23.

Callaway, E. M. and L. C. Katz (1993). "Photostimulation using caged glutamate reveals functional circuitry in living brain slices." *Proc Natl Acad Sci U S A* 90(16): 7661-5.

Campfield, L. A., F. J. Smith, et al. (1998). "Strategies and potential molecular targets for obesity treatment." *Science* 280(5368): 1383-7.

Cao, Y. and C. Dulac (2001). "Profiling brain transcription: neurons learn a lesson from yeast." *Curr Opin Neurobiol* 11(5): 615-20.

Carbon, M. and D. Eidelberg (2002). "Modulation of regional brain function by deep brain stimulation: studies with positron emission tomography." *Curr Opin Neurol* 15(4): 451-5.

Caterina, M. J. and D. Julius (2001). "The vanilloid receptor: a molecular gateway to the pain pathway." *Annu Rev Neurosci* 24: 487-517.

Caterina, M. J., M. A. Schumacher, et al. (1997). "The capsaicin receptor: a heat-activated ion channel in the pain pathway." *Nature* 389(6653): 816-24.

Clapham, D. E., L. W. Runnels, et al. (2001). "The TRP ion channel family." *Nat Rev Neurosci* 2(6): 387-396.

Crawley, J. N. (1999). "Behavioral phenotyping of transgenic and knockout mice: experimental design and evaluation of general health, sensory functions, motor abilities, and specific behavioral tests." *Brain Res* 835(1): 18-26.

Crawley, J. N. and R. Paylor (1997). "A proposed test battery and constellations of specific behavioral paradigms to investigate the behavioral phenotypes of transgenic and knockout mice." *Horm Behav* 31(3): 197-211.

DeFalco, J., M. Tomishima, et al. (2001). "Virus-assisted mapping of neural inputs to a feeding center in the hypothalamus." *Science* 291(5513): 2608-13.

Ding, S. and F. Sachs (2000). "Inactivation of P2X2 purinoceptors by divalent cations." *J Physiol* 522 Pt 2: 199-214.

Eberwine, J., J. E. Kacharmina, et al. (2001). "mRNA Expression Analysis of Tissue Sections and Single Cells." *J. Neurosci* 21: 8310-8314.

Follenzi, A., G. Sabatino, et al. (2002). "Efficient gene delivery and targeted expression to hepatocytes in vivo by improved lentiviral vectors." *Hum Gene Ther* 13(2): 243-60.

Friedman, J. M. and J. L. Halaas (1998). "Leptin and the regulation of body weight in mammals." *Nature* 395(6704): 763-70.

Frohman, M. A., M. K. Dush, et al. (1988). "Rapid production of full-length cDNAs from rare transcripts: amplification using a single gene-specific oligonucleotide primer." *Proc Natl Acad Sci U S A* 85(23): 8998-9002.

Georgopoulos, S., A. McKee, et al. (2002). "Generation and characterization of two transgenic mouse lines expressing human ApoE2 in neurons and glial cells." *Biochemistry* 41(30): 9293-301.

Gossen, M. and H. Bujard (2002). "Studying gene function in eukaryotes by conditional gene inactivation." *Annu Rev Genet* 36: 153-73.

Guler, A. D., H. Lee, et al. (2002). "Heat-evoked activation of the ion channel, TRPV4." *J Neurosci* 22(15): 6408-14.

Gusella, G. L., E. Fedorova, et al. (2002). "Lentiviral gene transduction of kidney." *Hum Gene Ther* 13(3): 407-14.

Herrera, P. L. (2000). "Adult insulin- and glucagon-producing cells differentiate from two independent cell lineages." *Development* 127(11): 2317-22.

Hille, B. (2001). *Ion channels of excitable membranes.* Sunderland, Sinauer.

Hoess, R. H. and K. Abremski (1984). "Interaction of the bacteriophage P1 recombinase Cre with the recombining site loxP." *Proc Natl Acad Sci U S A* 81(4): 1026-9.

Hoess, R. H. and K. Abremski (1985). "Mechanism of strand cleavage and exchange in the Cre-lox site-specific recombination system." *J Mol Biol* 181(3): 351-62.

Hofmann, S. L., D. W. Russell, et al. (1988). "Overexpression of low density lipoprotein (LDL) receptor eliminates LDL from plasma in transgenic mice." *Science* 239(4845): 1277-81.

Hogan, B., R. Beddington, et al. (1994). *Manipulating the Mouse Embryo.* New York, Cold Spring Harbor Laboratory Press.

Houdebine, L. M. (2002). "The methods to generate transgenic animals and to control transgene expression." *J Biotechnol* 98(2-3): 145-60.

Jackson, R. J., M. T. Howell, et al. (1990). "The novel mechanism of initiation of picornavirus RNA translation." *Trends Biochem Sci* 15(12): 477-83.

Jang, S. K., H. G. Krausslich, et al. (1988). "A segment of the 5' nontranslated region of encephalomyocarditis virus RNA directs internal entry of ribosomes during in vitro translation." *J Virol* 62(8): 2636-43.

Jerecic, J., C. H. Schulze, et al. (2001). "Impaired NMDA receptor function in mouse olfactory bulb neurons by tetracycline-sensitive NR1 (N598R) expression." *Brain Res Mol Brain Res* 94(1-2): 96-104.

Jiang, X., D. H. Rowitch, et al. (2000). "Fate of the mammalian cardiac neural crest." *Development* 127(8): 1607-16.

Jiang, Z., Z. Guo, et al. (2001). "Retinoblastoma gene promoter directs transgene expression exclusively to the nervous system." *J Biol Chem* 276(1): 593-600.

Kang, Y., C. S. Stein, et al. (2002). "In vivo gene transfer using a nonprimate lentiviral vector pseudotyped with Ross River Virus glycoproteins." *J Virol* 76(18): 9378-88.

Kaplan, J. H., B. Forbush, 3rd, et al. (1978). "Rapid photolytic release of adenosine 5'-triphosphate from a protected analogue: utilization by the Na:K pump of human red blood cell ghosts." *Biochemistry* 17(10): 1929-35.

Kobinger, G. P., D. J. Weiner, et al. (2001). "Filoviruspseudotyped lentiviral vector can efficiently and stably transduce airway epithelia in vivo." *Nat Biotechnol* 19(3): 225-30.

Kozloski, J., F. Hamzei-Sichani, et al. (2001). "Stereotyped position of local synaptic targets in neocortex." *Science* 293(5531): 868-72.

Kugler, S., L. Meyn, et al. (2001). "Neuron-specific expression of therapeutic proteins: evaluation of different cellular promoters in recombinant adenoviral vectors." *Mol Cell Neurosci* 17(1): 78-96.

Kuner, T. and G. J. Augustine (2000). "A genetically encoded ratiometric indicator for chloride: capturing chloride transients in cultured hippocampal neurons." *Neuron* 27(3): 447-59.

Lavon, I., I. Goldberg, et al. (2000). "High susceptibility to bacterial infection, but no liver dysfunction, in mice compromised for hepatocyte NF-kappaB activation." *Nat Med* 6(5): 573-7.

Lee, P., G. Morley, et al. (1998). "Conditional lineage ablation to model human diseases." *Proc Natl Acad Sci U S A* 95(19): 11371-6.

Leighton, P. A., K. J. Mitchell, et al. (2001). "Defining brain wiring patterns and mechanisms through gene trapping in mice." *Nature* 410(6825): 174-9.

Lewandoski, M. (2001). "Conditional Control of Gene Expression in the Mouse." *Nature Review Genetics* 2(10): 743-755.

Liu, M., M. C. Liu, et al. (2003). "Versatile regulation of cytosolic Ca2+ by vanilloid receptor I in rat dorsal root ganglion neurons." *J Biol Chem* 278(7): 5462-72.

Lois, C., E. J. Hong, et al. (2002). "Germline transmission and tissue-specific expression of transgenes delivered by lentiviral vectors." *Science* 295(5556): 868-72.

Lowenstein, P. R. and L. W. Enquist, Eds. (1996). *Protocols for gene transfer in neuroscience.* Chichester—N.Y., John Wiley.

Makinae, K., T. Kobayashi, et al. (2000). "Structure of the mouse glutamate decarboxylase 65 gene and its promoter: preferential expression of its promoter in the GABAergic neurons of transgenic mice." *J Neurochem* 75(4): 1429-37.

Marriott, G. (1994). "Caged protein conjugates and light-directed generation of protein activity: preparation, photoactivation, and spectroscopic characterization of caged G-actin conjugates." *Biochemistry* 33(31): 9092-7.

Marshall, I. C., D. E. Owen, et al. (2003). "Activation of vanilloid receptor 1 by resiniferatoxin mobilizes calcium from inositol 1,4,5-trisphosphate-sensitive stores." *Br J Pharmacol* 138(1): 172-6.

Matsui, T., L. Li, et al. (2002). "Phenotypic spectrum caused by transgenic overexpression of activated Akt in the heart." *J Biol Chem* 277(25): 22896-901.

McCray, J. A. and D. R. Trentham (1989). "Properties and uses of photoreactive caged compounds." *Annu Rev Biophys Biophys Chem* 18: 239-70.

McKemy, D. D., W. M. Neuhausser, et al. (2002). "Identification of a cold receptor reveals a general role for TRP channels in thermosensation." *Nature* 416(6876): 52-8.

Mezey, E., Z. E. Toth, et al. (2000). "Distribution of mRNA for vanilloid receptor subtype 1 (VR1), and VR1-like immunoreactivity, in the central nervous system of the rat and human." *Proc Natl Acad Sci U S A* 97(7): 3655-60.

Miesenböck, G., D. A. De Angelis, et al. (1998). "Visualizing secretion and synaptic transmission with pH-sensitive green fluorescent proteins." *Nature* 394(6689): 192-5.

Miyawaki, A., O. Griesbeck, et al. (1999). "Dynamic and quantitative Ca2+ measurements using improved cameleons." *Proc Natl Acad Sci U S A* 96(5): 2135-40.

Miyawaki, A., J. Llopis, et al. (1997). "Fluorescent indicators for Ca2+ based on green fluorescent proteins and calmodulin." *Nature* 388(6645): 882-7.

Miyazaki, J., S. Takaki, et al. (1989). "Expression vector system based on the chicken beta-actin promoter directs efficient production of interleukin-5." *Gene* 79(2): 269-77.

Mochizuki, H., J. P. Schwartz, et al. (1998). "High-titer human immunodeficiency virus type 1-based vector systems for gene delivery into nondividing cells." *J Virol* 72(11): 8873-83.

Montell, C., L. Birnbaumer, et al. (2002). "The TRP channels, a remarkably functional family." *Cell* 108(5): 595-8.

Moriyoshi, K., L. J. Richards, et al. (1996). "Labeling neural cells using adenoviral gene transfer of membrane-targeted GFP." *Neuron* 16(2): 255-60.

Nagai, T., A. Sawano, et al. (2001). "Circularly permuted green fluorescent proteins engineered to sense Ca2+." *Proc Natl Acad Sci U S A* 98(6): 3197-202.

Nakai, J., M. Ohkura, et al. (2001). "A high signal-to-noise Ca2+ probe composed of a single green fluorescent protein." *Nat Biotechnol* 19(2): 137-141.

Naldini, L., U. Blomer, et al. (1996). "In vivo gene delivery and stable transduction of nondividing cells by a lentiviral vector." *Science* 272(5259): 263-7.

Nery, S., G. Fishell, et al. (2002). "The caudal ganglionic eminence is a source of distinct cortical and subcortical cell populations." *Nat Neurosci* 5(12): 1279-87.

Newbolt, A., R. Stoop, et al. (1998). "Membrane topology of an ATP-gated ion channel (P2X receptor)." *J Biol Chem* 273(24): 15177-82.

Nicolelis, M. A. and S. Ribeiro (2002). "Multielectrode recordings: the next steps." *Curr Opin Neurobiol* 12(5): 602-6.

North, R. A. (2002). "Molecular physiology of P2X receptors." *Physiol Rev* 82(4): 1013-67.

Ozturk-Winder, F., M. Renner, et al. (2002). "The murine whey acidic protein promoter directs expression to human mammary tumors after retroviral transduction." *Cancer Gene Ther* 9(5): 421-31.

Peier, A. M., A. Moqrich, et al. (2002). "A TRP channel that senses cold stimuli and menthol." *Cell* 108(5): 705-15.

Peterlin, Z. A., J. Kozloski, et al. (2000). "Optical probing of neuronal circuits with calcium indicators." *Proc Natl Acad Sci U S A* 97(7): 3619-24.

Rapp, G. (1998). "Flash lamp-based irradiation of caged compounds." *Methods Enzymol* 291: 202-22.

Rockenstein, E., M. Mallory, et al. (2002). "Differential neuropathological alterations in transgenic mice expressing alpha-synuclein from the platelet-derived growth factor and Thy-1 promoters." *J Neurosci Res* 68(5): 568-78.

Roscilli, G., C. D. Rinaudo, et al. (2002). "Long-term and tight control of gene expression in mouse skeletal muscle by a new hybrid human transcription factor." *Mol Ther* 6(5): 653-63.

Saam, J. R. and J. I. Gordon (1999). "Inducible gene knockouts in the small intestinal and colonic epithelium." *J Biol Chem* 274(53): 38071-82.

Sakai, N., J. Thome, et al. (2002). "Inducible and brain region-specific CREB transgenic mice." *Mol Pharmacol* 61(6): 1453-64.

Sandberg, R., R. Yasuda, et al. (2000). "Regional and strain-specific gene expression mapping in the adult mouse brain." *Proc Natl Acad Sci U S A* 97(20): 11038-11043.

Sankaranarayanan, S. and T. A. Ryan (2001). "Calcium accelerates endocytosis of vSNAREs at hippocampal synapses." *Nature Neurosci*.

Schwartz, M. W., S. C. Woods, et al. (2000). "Central nervous system control of food intake." *Nature* 404(6778): 661-71.

Shah, K., Y. Liu, et al. (1997). "Engineering unnatural nucleotide specificity for Rous sarcoma virus tyrosine kinase to uniquely label its direct substrates." *Proc Natl Acad Sci U S A* 94(8): 3565-70.

Shimozono, S., T. Fukano, et al. (2002). "Confocal imaging of subcellular Ca2+ concentrations using a dual-excitation ratiometric indicator based on green fluorescent protein." *Sci STKE* 2002(125): PL4.

Soriano, P. (1999). "Generalized lacZ expression with the ROSA26 Cre reporter strain." *Nat Genet* 21(1): 70-1.

Srinivas, S., T. Watanabe, et al. (2001). "Cre reporter strains produced by targeted insertion of EYFP and ECFP into the ROSA26 locus." *BMC Dev Biol* 1(1): 4.

St John, P. A., W. M. Kell, et al. (1986). "Analysis and isolation of embryonic mammalian neurons by fluorescence-activated cell sorting." *J Neurosci* 6(5): 1492-512.

Stanford, W. L., J. B. Cohn, et al. (2001). "Gene-Trap Mutagenesis: Past, Present and Beyond." *Nature Review Genetics* 2(10): 756-768.

Takamori, S., J. S. Rhee, et al. (2001). "Identification of differentiation-associated brain-specific phosphate transporter as a second vesicular glutamate transporter (VGLUT2)." *J Neurosci* 21(22): RC182.

Tobin, D. M., D. M. Madsen, et al. (2002). "Combinatorial expression of TRPV channel proteins defines their sensory functions and subcellular localization in C. elegans neurons." *Neuron* 35(2): 307.

Tomomura, M., D. S. Rice, et al. (2001). "Purification of Purkinje cells by fluorescence-activated cell sorting from transgenic mice that express green fluorescent protein." *Eur J Neurosci* 14(1): 57-63.

Townley, D. J., B. J. Avery, et al. (1997). "Rapid sequence analysis of gene trap integrations to generate a resource of insertional mutations in mice." *Genome Res* 7(3): 293-8.

Valera, S., N. Hussy, et al. (1994). "A new class of ligand-gated ion channel defined by P2x receptor for extracellular ATP." *Nature* 371(6497): 516-9.

Vallier, L., J. Mancip, et al. (2001). "An efficient system for conditional gene expression in embryonic stem cells and in their in vitro and in vivo differentiated derivatives." *Proc Natl Acad Sci U S A* 98(5): 2467-72.

Walker, J. W., J. A. McCray, et al. (1986). "Photolabile protecting groups for an acetylcholine receptor ligand. Synthesis and photochemistry of a new class of o-nitrobenzyl derivatives and their effects on receptor function." *Biochemistry* 25(7): 1799-805.

Walker, J. W., G. P. Reid, et al. (1989). "Synthesis and properties of caged nucleotides." *Methods Enzymol* 172: 288-301.

Walpole, C. S., S. Bevan, et al. (1996). "Similarities and differences in the structure-activity relationships of capsaicin and resiniferatoxin analogues." *J Med Chem* 39(15): 2939-52.

Walpole, C. S., R. Wrigglesworth, et al. (1993). "Analogues of capsaicin with agonist activity as novel analgesic agents; structure-activity studies. 1. The aromatic "A-region"." *J Med Chem* 36(16): 2362-72.

Watson, D. J., G. P. Kobinger, et al. (2002). "Targeted transduction patterns in the mouse brain by lentivirus vectors pseudotyped with VSV, Ebola, Mokola, LCMV, or MuLV envelope proteins." *Mol Ther* 5(5 Pt 1): 528-37.

Wilcox, M., R. W. Viola, et al. (1990). "Synthesis of photolabile "precursors" of amino acid neurotransmitters." *J. Org. Chem.* 55: 1585-1589.

Wool-Lewis, R. J. and P. Bates (1998). "Characterization of Ebola virus entry by using pseudotyped viruses: identification of receptor-deficient cell lines." *J Virol* 72(4): 3155-60.

Yamaoka, T., K. Yoshino, et al. (2002). "Transgenic expression of FGF8 and FGF10 induces transdifferentiation of pancreatic islet cells into hepatocytes and exocrine cells." *Biochem Biophys Res Commun* 292(1): 138-43.

Zambrowicz, B. P., A. Imamoto, et al. (1997). "Disruption of overlapping transcripts in the ROSA beta geo 26 gene trap strain leads to widespread expression of beta-galactosidase in mouse embryos and hematopoietic cells." *Proc Natl Acad Sci U S A* 94(8): 3789-94.

Zemelman, B. V., G. A. Lee, et al. (2002). "Selective photostimulation of genetically chARGed neurons." *Neuron* 33(1): 15-22.

Zemelman, B. V. and G. Miesenböck (2001). "Genetic schemes and schemata in neurophysiology." *Curr Opin Neurobiol* 11: 409-14.

Zemelman, B. V., N. Nesnas, et al. (2003). "Photochemical gating of heterologous ion channels: remote control over genetically designated populations of neurons." *Proc Natl Acad Sci U S A* 100(3): 1352-7.

Zinyk, D. L., E. H. Mercer, et al. (1998). "Fate mapping of the mouse midbrain-hindbrain constriction using a site-specific recombination system." *Curr Biol* 8(11): 665-8.

Zufferey, R., D. Nagy, et al. (1997). "Multiply attenuated lentiviral vector achieves efficient gene delivery in vivo." *Nat Biotechnol* 15(9): 871-5.

CHART 1

| | Neuronal pathway known | | |
|---|---|---|---|
| Cell | Tissue | Animal | Human |

Tissue column:
Stimulate neuronal pathway
↓
Identify and profile stimulated neurons →

Animal column:
Introduce ligand-gated ion channels into neurons
↓
Activate neurons
↓
Generate behavioral phenotype
↓
Harvest neurons ← (to Tissue)

Cell column:
Culture neurons
↓
Identify compounds that activate or silence neurons selectively → Test compounds on healthy animals
↓
Correct behavioral phenotype pharmacologically → Drug thetapy in humans
↓
Correct behavioral phenotype through gene therapy → Gene therapy in humans

CHART 2

| | Neuronal pathway not known | | |
|---|---|---|---|
| Cell | Tissue | Animal | Human |

Animal column:
Introduce ligand-gated ion channels into neurons
↓
Activate neurons
↓
Generate behavioral phenotype
↓
Identify stimulated neurons histologically
↓
Harvest neurons ←

Cell column:
Culture neurons
↓
Identify compounds that activate or silence neurons selectively → Test compounds on healthy animals
↓
Correct behavioral phenotype pharmacologically → Drug therapy in humans
↓
Correct behavioral phenotype through gene therapy → Gene therapy in humans

The invention claimed is:

1. A method for activation of eukaryotic target cells, comprising the steps of:
   a. sensitizing target cells by expressing a heterologous stimulus-gated ion channel in those target cells, wherein the heterologous stimulus-gated ion channel is one that does not naturally occur in the target cell in the absence of human intervention, and
   b. applying a stimulus to the sensitized target cells to trigger the ion channel, and thereby activate the target cells to induce a response characteristic of the target cell, wherein the activation results in polarization or depolarization when the target cell is a neuronal cell, commencement or termination of secretion from the target cell when the target cell is a secretory cell; contraction or relaxation when the target cell is a muscle or other contractile cell, or a sensory response when the target cell is a sensory receptor.

2. The method of claim 1, wherein the stimulus-gated ion channel is a ligand-gated ion channel.

3. The method of claim 2, wherein the stimulus is applied to the ligand-gated ion channel by exposing the target cells to a ligand that gates the ion channel.

4. The method of claim 2, wherein the stimulus-gated ion channel is selected from the group consisting of TRPV1 and TRPM8.

5. The method of claim 4, wherein the stimulus-gated ion channel is TRPV1 and the target cells are stimulated by contacting the cells with capsaicin.

6. The method of claim 4, wherein the stimulus-gated ion channel is TRPM8 and the target cells are stimulated by contacting the cells with menthol or icilin.

7. The method of claim 2, wherein the stimulus-gated ion channel is P2X2.

8. The method of claim 7, wherein the target cells are stimulated by contacting the cells with ATP.

9. The method of claim 3, wherein the ligand is initially in the form of a photolabile caged ligand, and wherein the stimulus is applied to the ligand-gated ion channel upon exposure of the photolabile caged ligand to light.

10. The method of claim 9, wherein the photolabile caged ligand is exposed to pulses of light.

11. The method of claim 9, wherein the stimulus-gated ion channel is TRPV1 and the ligand is DMNB-capsaicin.

12. The method of claim 9, wherein the stimulus-gated ion channel is TRPM8 and the ligand is DMNB-menthol.

13. The method of claim 9, wherein the stimulus-gated ion channel is P2X2, and the ligand is DMNPE-ATP.

14. The method of claim 1, wherein the expression of the heterologous stimulus-gated ion channel is controlled to occur only within a defined cell-type.

15. The method of claim 14, wherein the expression is controlled by an inducible or repressible promoter.

16. The method of claim 15, wherein the promoter is chosen from among promoters responding to steroids, antibiotics, 4-OH tamoxifen, or heavy metals.

17. The method of claim 14, wherein the expression of the heterologous stimulus-gated ion channel is controlled by a cell-type specific promoter.

18. The method of claim 14, wherein the expression of the heterologous stimulus-gated ion channel is controlled by a secondary cell-type specific control element.

19. The method of claim 18, wherein the secondary cell-type specific control element comprises a loxP-stop-loxP sequence disposed between a genetic sequence encoding the heterologous stimulus-gated ion channel and a promoter associated with the heterologous stimulus-gated ion channel, and a cell-type specific promoter, said cell-type specific control element controlling expression of a genetic sequence encoding bacterial Cre protein.

20. The method of claim 1, wherein the stimulus-gated ion channel is TRPV1 and the target cells are stimulated by contacting the cells with heat or radiation.

21. The method of claim 1, wherein the stimulus-gated ion channel is TRPM8 and the target cells are stimulated by contacting the cells with cold.

22. The method of claim 1, wherein the target cells are activated in vitro.

23. The method of claim 1, wherein the target cells are activated in vivo.

24. A method for mapping neuronal and neuroendocrine pathways comprising the steps of:
   (a) sensitizing target cells associated with the neuronal or neuroendocrine pathway by expressing a heterologous stimulus-gated ion channel in those target cells, wherein the heterologous stimulus-gated ion channel is one that does not naturally occur in the target cells in the absence of human intervention, and
   (b) applying a stimulus to the sensitized target cells to trigger the ion channel, and thereby activate the target cells to induce a response characteristic of the target cells that is part of the neuronal or neuroendocrine pathway; and wherein the activation results in polarization or depolarization when the target cell is a neuronal cell, commencement or termination of secretion from the target cell when the target cell is a secretory cell, contraction or relaxation when the target cell is a muscle or other contractile cell, or a sensory response when the target cell is a sensory receptor
   (c) monitoring the response of putatively downstream cells to the activation of the sensitized cells, wherein observation of a response in downstream cells indicates that these cells are, in fact, downstream from the sensitized cells in a neuronal or neuroendocrine pathway.

25. A method for evaluating cells of a specific cell type to determine if the cells are involved in producing a phenotype associated with a disease or condition comprising the steps of:
   (a) sensitizing target cells by expressing a heterologous stimulus-gated ion channel in those target cells, wherein the heterologous stimulus-gated ion channel is one that does not naturally occur in the target cells in the absence of human intervention, and (b) applying a stimulus to the sensitized target cells to trigger the ion channel, and thereby activate the target cells to induce a response characteristic of the target cells; and wherein the activation results in polarization or depolarization when the target cell is a neuronal cell, commencement or termination of secretion from the target cell when the target cell is a secretory cell, contraction or relaxation when the target cell is a muscle or other contractile cell, or a sensory response when the target cell is a sensory receptor (c) observing the effect, if any, of triggering the ion channel, wherein an effect corresponding to the appearance or reduction of the phenotype indicates an involvement of the cell type with the disease or condition.

26. A method for identifying cells of a specific cell type to determine if the cells are involved in producing a phenotype associated with a disease or condition comprising the steps of:

(a) sensitizing target cells by expressing a heterologous stimulus-gated ion channel in those target cells, wherein the heterologous stimulus-gated ion channel is one that does not naturally occur in the target cells in the absence of human intervention, and (b) applying a stimulus to the sensitized target cells to trigger the ion channel, and thereby activate the target cells to induce a response characteristic of the target cells; and wherein the activation results in polarization or depolarization when the target cell is a neuronal cell, commencement or termination of secretion from the target cell when the target cell is a secretory cell, contraction or relaxation when the target cell is a muscle or other contractile cell, or a sensory response when the target cell is a sensory receptor (c) observing the effect, if any, of triggering the ion channel, wherein an effect corresponding to the appearance or reduction of the phenotype indicates an involvement of the cell type with the disease or condition.

27. The method of claim 1, wherein the target cells are neuronal cells.

28. The method of claim 1, wherein the target cells are secretory cells.

29. The method of claim 1, wherein the target cells are muscle or other contractile cells.

30. The method of claim 1, wherein the target cells are sensory receptor cells.

31. The method of claim 30, wherein the stimulus-gated ion channel is selected from the group consisting of TRPV1 and TRPM8.

32. The method of claim 31, wherein the stimulus-gated ion channel is TRPV1 and the target cells are stimulated by contacting the cells with capsaicin.

33. The method of claim 31, wherein the stimulus-gated ion channel is TRPM8 and the target cells are stimulated by contacting the cells with menthol or icilin.

34. The method of claim 30, wherein the stimulus-gated ion channel is P2X2.

35. The method of claim 33, wherein the target cells are stimulated by contacting the cells with ATP.

36. The method of claim 29, wherein the stimulus-gated ion channel is selected from the group consisting of TRPV1 and TRPM8.

37. The method of claim 36, wherein the stimulus-gated ion channel is TRPV1 and the target cells are stimulated by contacting the cells with capsaicin.

38. The method of claim 36, wherein the stimulus-gated ion channel is TRPM8 and the target cells are stimulated by contacting the cells with menthol or icilin.

39. The method of claim 29, wherein the stimulus-gated ion channel is P2X2.

40. The method of claim 39, wherein the target cells are stimulated by contacting the cells with ATP.

41. The method of claim 28, wherein the stimulus-gated ion channel is selected from the group consisting of TRPV1 and TRPM8.

42. The method of claim 41, wherein the stimulus-gated ion channel is TRPV1 and the target cells are stimulated by contacting the cells with capsaicin.

43. The method of claim 41, wherein the stimulus-gated ion channel is TRPM8 and the target cells are stimulated by contacting the cells with menthol or icilin.

44. The method of claim 28, wherein the stimulus-gated ion channel is P2X2.

45. The method of claim 44, wherein the target cells are stimulated by contacting the cells with ATP.

46. The method of claim 27, wherein the stimulus-gated ion channel is selected from the group consisting of TRPV1 and TRPM8.

47. The method of claim 46, wherein the stimulus-gated ion channel is TRPV1 and the target cells are stimulated by contacting the cells with capsaicin.

48. The method of claim 46, wherein the stimulus-gated ion channel is TRPM8 and the target cells are stimulated by contacting the cells with menthol or icilin.

49. The method of claim 27, wherein the stimulus-gated ion channel is P2X2.

50. The method of claim 49, wherein the target cells are stimulated by contacting the cells with ATP.

* * * * *

UNITED STATES PATENT AND TRADEMARK OFFICE
CERTIFICATE OF CORRECTION

PATENT NO. : 7,883,846 B2
APPLICATION NO. : 10/452879
DATED : February 8, 2011
INVENTOR(S) : Miesenbock et al.

It is certified that error appears in the above-identified patent and that said Letters Patent is hereby corrected as shown below:

Column 46, Claim 24, Line 51, should read - ...target cell is a sensory receptor and; ...

Column 47, Claim 25, Line 10, should read - ...target cell is a sensory receptor and; ...

Column 47, Claim 26, Line 33, should read - ...target cell is a sensory receptor and; ...

Column 48, Claim 35, Line 9, should read - The method of claim 34, wherein the target cells are ...

Signed and Sealed this
Fourteenth Day of June, 2011

David J. Kappos
*Director of the United States Patent and Trademark Office*

SEQUENCE LISTING

<160> NUMBER OF SEQ ID NOS: 8

<210> SEQ ID NO 1
<211> LENGTH: 2847
<212> TYPE: DNA
<213> ORGANISM: Rattus norvegicus

<400> SEQUENCE: 1

-continued

```
cagctccaag gcacttgctc catttggggt gtgcctgcac ctagctggtt gcaaattggg      60
ccacagagga tctggaaagg atggaacaac gggctagctt agactcagag gagtctgagt     120
ccccacccca agagaactcc tgcctggacc ctccagacag agaccctaac tgcaagccac     180
ctccagtcaa gccccacatc ttcactacca ggagtcgtac ccggcttttt gggaagggtg     240
actcggagga ggcctctccc ctggactgcc ttatgagga aggcgggctg gcttcctgcc     300
ctatcatcac tgtcagctct gttctaacta tccagaggcc tggggatgga cctgccagtg     360
tcaggccgtc atcccaggac tccgtctccg ctggtgagaa gccccgagg ctctatgatc      420
gcaggagcat cttcgatgct gtggctcaga gtaactgcca ggagctggag agcctgctgc     480
ccttcctgca gaggagcaag aagcgcctga ctgacgcga gttcaaagac ccagagacag     540
gaaagacctg tctgctaaaa gccatgctca atctgcacaa tgggcagaat gacaccatcg     600
ctctgctcct ggacgttgcc cggaagacag acagcctgaa gcagtttgtc aatgccagct     660
acacagacag ctactacaag ggccagacag cactgcacat tgccattgaa cggcggaaca     720
tgacgctggt gaccctcttg gtggagaatg gagcagatgt ccaggctgcg gctaacgggg     780
acttcttcaa gaaaaccaaa gggaggcctg gcttctactt tggtgagctg ccctgtccc      840
tggctgcgtg caccaaccag ctggccattg tgaagttcct gctgcagaac tcctggcagc     900
ctgcagacat cagcgcccgg gactcagtgg gcaacacggt gcttcatgcc ctggtggagg     960
tggcagataa cacagttgac aacaccaagt tcgtgacaag catgtacaac gagatcttga    1020
tcctgggggc caaactccac cccacgctga agctggaaga gatcaccaac aggaaggggc    1080
tcacgccact ggctctggct gctagcagtg gaagatcgg ggtcttggcc tacattctcc     1140
agagggagat ccatgaaccc gagtgccgac acctatccag gaagttcacc gaatgggcct    1200
atgggccagt gcactcctcc ctttatgacc tgtcctgcat tgacacctgt gaaaagaact    1260
cggttctgga ggtgatcgct acagcagca gtgagacccc taaccgtcat gacatgcttc     1320
tcgtggaacc cttgaaccga ctcctacagg acaagtggga cagatttgtc aagcgcatct    1380
tctacttcaa cttcttcgtc tactgcttgt atatgatcat cttcaccgcg gctgcctact    1440
atcggcctgt ggaaggcttg ccccctata agctgaaaaa caccgttggg gactatttcc     1500
gagtcaccgg agagatcttg tctgtgtcag gaggagtcta cttcttcttc cgagggattc    1560
aatatttcct gcagaggcga ccatccctca gagtttgtt tgtggacagc tacagtgaga     1620
tacttttctt tgtacagtcg ctgttcatgc tggtgtctgt ggtactgtac ttcagccaac    1680
gcaaggagta tgtggcttcc atggtgttct ccctggccat gggctggacc aacatgctct    1740
actatacccg aggattccag cagatgggca tctatgctgt catgattgag aagatgatcc    1800
tcagagacct gtgccggttt atgttcgtct acctcgtgtt cttgtttgga ttttccacag    1860
ctgtggtgac actgattgag gatgggaaga ataactctct gcctatggag tccacaccac    1920
acaagtgccg ggggtctgcc tgcaagccag gtaactctta caacagcctg tattccacat    1980
gtctggagct gttcaagttc accatcggca tgggcgacct ggagttcact gagaactacg    2040
acttcaaggc tgtcttcatc atcctgttac tggcctatgt gattctcacc tacatccttc    2100
tgctcaacat gctcattgct ctcatgggtg agaccgtcaa caagattgca caagagagca    2160
agaacatctg gaagctgcag agagccatca ccatcctgga tacagagaag agcttcctga    2220
agtgcatgag gaaggccttc cgctctggca agctgctgca ggtggggttc actcctgacg    2280
gcaaggatga ctaccggtgg tgtttcaggg tggacgaggt aaactggact acctggaaca    2340
```

```
ccaatgtggg tatcatcaac gaggacccag gcaactgtga gggcgtcaag cgcaccctga   2400
gcttctccct gaggtcaggc cgagtttcag ggagaaactg gaagaacttt gccctggttc   2460
cccttctgag ggatgcaagc actcgagata gacatgccac ccagcaggaa gaagttcaac   2520
tgaagcatta tacgggatcc cttaagccag aggatgctga ggttttcaag gattccatgg   2580
tcccagggga gaataatgg acactatgca gggatcaatg cggggtcttt gggtggtctg    2640
cttagggaac cagcagggtt gacgttatct gggtccactc tgtgcctgcc taggcacatt   2700
cctaggactt cggcgggcct gctgtgggaa ctgggaggtg tgtgggaatt gagatgtgta   2760
tccaaccatg atctccaaac atttggcttt caactcttta tggactttat aaacagagt    2820 gaatggcaaa tctctacttg gacacat                                       2847
```

<210> SEQ ID NO 2
<211> LENGTH: 4184
<212> TYPE: DNA
<213> ORGANISM: Rattus norvegicus

<400> SEQUENCE: 2

```
gtgctctaaa gagaagctct tggctgtttg agcagctcca cggcaagatg tccttcgagg     60
gagccaggct cagcatgagg agccgcagaa atggaactct gggcagcacc cggacccctgt   120 actccagcgt gtctcggagc acagacgtgt cctacagtga aagtgatttg gtgaattta    180 ttcaggcaaa ttttaaaaaa cgagaatgcg tcttctttac cagagactcc aaggccatgg    240
agagcatatg caagtgtggt tatgcccaga gccagcatat cgaaggcacc cagatcaacc    300
aaaatgagaa gtggaactac aaaaaacaca ccaaggagtt tccaacagac gccttgggg    360 acattcagtt tgagactctg gggaagaaag gcaagtactt acgcttatcc tgtgacacgg    420
actctgaaac cctctacgaa ctgctgaccc agcactggca cctcaaaaca cccaacctgg    480
tcatctcagt gacgggtgga gccaaaaact ttgctttgaa gccacgcatg cgcaaaatct    540
tcagtcggct gatctacatc gctcagtcta aggggcatg gattcttacc ggaggcactc    600
attacggtct gatgaagtac ataggtgaag tggtgaggga taacaccatc agcaggaact    660
cggaagagaa catcgtggcc attggcatag cggcctgggg catggtctcc aacagggaca    720
ccctcatcag gaattgtgat gatgagggac attttttcagc tcaatatatc atggatgact    780
tcatgagaga tcctctctac atcctggaca acaatcatac ccacctgctg cttgtggaca    840
acggttgtca tggacacccc acggtggaag ccaaacttcg gaatcagctg agaagtaca    900 tctctgagcg caccagtcaa gattccaact atggtggtaa gatccccatc gtgtgttttg    960
cccagggagg tggaagagaa actttgaaag ccatcaacac ctctgtcaaa agtaagatcc   1020
cctgtgtggt ggtggaaggc tcggggcaga ttgccgatgt gattgccagc ctggtggagg   1080
tagaggatgt tttaacctct tccatggtca agagaagct ggtacggttt ttaccccgca    1140
ctgtgtcccg gctgcctgaa gaggagattg agagctggat caaatggctc aaagaaattc   1200
ttgagagccc ccacctcctc acggtcatca agatggagga ggctggagac gaggtcgtga   1260
gcagcgccat ttcctacgcg ctgtacaaag ccttcagcac taatgaacaa gacaaggaca   1320
actggaacgg acagctgaag cttctgctgg agtggaacca actggacctt gccagtgatg   1380
agatcttcac ccatgaccgc cgctgggagt ctgccgacct tcaggaagtc atgttcacgg   1440
ccctcataaa ggacaggccc aagtttgtcc gcctcttcct ggagaatggc ctcaacctgc   1500
agaagttcct caccaatgaa gtcctcacgg agctcttctc cacccacttc agcacccctag  1560 tgtaccggaa cctgcagatc gccaagaact cctacaacga tgcactcctt acctttgtct   1620
```

```
ggaagttggt ggcaaacttc cgtagaagct tctggaaaga ggacagaagc agcagggagg    1680
acttggatgt ggaactccat gatgcatctc tcaccacccg gcaccccctg caggctcttt    1740
tcatctgggc cattcttcag aacaagaagg aactctccaa ggtcatctgg gagcaaacca    1800
aaggctgtac tctggccgcc ttgggggcca gcaaacttct gaagaccctg gccaaagtta    1860
agaatgatat caacgcagct ggggaatctg aggaactggc taatgagtat gagacccgag    1920
cagtggagtt gttcactgag tgttacagca gtgatgagga cttggcagaa cagctactgg    1980
tctactcttg tgaagcctgg ggtgggagca actgtctgga gctggcggtg gaggctacgg    2040
accagcattt cattgctcag cctggggtcc agaatttcct ttctaagcaa tggtatggag    2100
agatttcccg agacacgaag aactggaaga ttatcctgtg tctgttcatc atcccctgg     2160 tgggctgtgg cctcgtatcg tttaggaaga agcccattga caagcacaag aagctgctct    2220
ggtactacgt ggccttcttc acttcgccct tcgtggtctt ctcctggaac gtggtcttct    2280
acatcgcctt cctcctgctg tttgcgtatg tgctgctcat ggacttccac tcggtgccac    2340
acacccccga gctgatcctc tatgccctgg tcttcgtcct cttctgtgat gaagtgaggc    2400
agtggtacat gaacggagtg aattatttca ccgacctatg gaacgttatg gacacactgg    2460
gacttttcta cttcatagcg ggtattgtat tccggcttca ctcttcaaat aaaagctctt    2520
tgtactccgg gcgagtcatt ttctgtctgg attacattat attcactcta aggctcatcc    2580 acatttttcac cgtgagcagg aacctgggac ccaagattat aatgctgcag cggatgctca    2640
tcgacgtttt cttcttcttg tttctctttg ctgtgtggat ggtggccttc ggcgtagcca    2700
gacaggggat ccttaggcaa aatgaacagc gctggaggtg gatcttccgc tctgtcatct    2760
atgagcccta cctggccatg tttggccagg tgcccagtga tgtggacagt accacatatg    2820
acttctccca ctgcaccttc tcgggaaatg agtccaagcc actgtgcgtg gagctagatg    2880
aatacaatct gccccgcttc cctgagtgga tcaccatccc actagtgtgc atctacatgc    2940
tctccaccaa catccttctg gtcaatctcc tggtcgccat gttttggctac acggtgggca    3000 ttgtgcagga gaacaacgat caggtctgga gttccagcg gtacttcctg gtgcaggagt    3060
actgcaaccg cctcaacatc cccttcccct tcgtcgtctt cgcttacttc tacatggtgg    3120
tcaagaagtg tttcaaatgc tgctgtaaag agaagaacac ggagtcttct gcctgctgtt    3180
tcagaaatga ggacaacgag actttggcgt gggagggcgt catgaaggag aattaccttg    3240
tcaagatcaa cacgcaaggcc aacgacaacg cagaggagag gaggcatcgg ttcagacaac    3300
tggacacaaa gcttaatgat ctcaaaggtc ttctgaaaga gattgctaat aaaatcaaat    3360
aaggcaggcg actgctcatg gagagaagtc aaattgcaat aagatcaaat caaacacctg    3420
gatttggagg ctcgtgggac tctgataaac aatactgcta ttgacttcta aaggagacat    3480
ttccaggtcc ctgggcacaa agtggatgag tcatagtcac cctcaagggc ataggtcagg    3540
gaccaaagtg tacagagaac tgtgcacaag aagaggagtg caaaggttcc tccatgaagg    3600
tgcctgtgct gtctgcatct cggagccttg aactgatgct gaaggtttaa gtgatgacac    3660
acctttccca ccctcgtctc atgcacctcc catgactgtg accctggccc tgattttaca    3720
cctacactgc tattgtgttt atttcctact gtcccctttc tgcattgtat gatgaattca    3780
tcgacatagg tcagagtcct acaccacccc aaagaaaagt caggccggat gctaaaatac    3840
cctggggcaa cctctccttt ctcacatgtc aaacgtggga ggtgtgtgtg tggggggggc    3900
acacggaggc agtgacttct ttctctgggg ctctccagga ctcctgctga aggaacccctt   3960
```

-continued

| | |
|---|---|
| gagagccgta ccttgctcct tttgttttg ggagtgtgcc tctcctccat tctctcatta | 4020 |
| tttccccatt gagaatagca aatggatctc acaggaggtt agaggagcac aaaaatgtat | 4080 |
| ggaaacggcc tcccactcac agcccttgct cacacttccg tgtgtttgct caatcccagc | 4140 |
| cttttctatg catgctacac ttcactttta aaaaaaaaaa aaaa | 4184 |

<210> SEQ ID NO 3
<211> LENGTH: 1831
<212> TYPE: DNA
<213> ORGANISM: Rattus norvegicus

<400> SEQUENCE: 3

| | |
|---|---|
| gccgctgcac agccccggct tcccgcgggg gcggccatgg tccggcgctt ggcccggggc | 60 |
| tgctggtccg cgttctggga ctacgagacg cctaaggtga tcgtggtgcg gaatcggcgc | 120 |
| ctgggattcg tgcaccgcat ggtgcagctt tcatcctgc tttacttcgt gtggtacgtc | 180 |
| ttcatcgtgc agaaaagcta ccaggacagc gagaccggac cggagagctc catcatcacc | 240 |
| aaagtcaagg ggatcaccat gtcggaagac aaagtgtggg acgtggagga atacgtaaag | 300 |
| ccccccggagg ggggcagtgt agtcagcatc atcaccagga tcgaggttac cccttcccag | 360 |
| accttgggaa catgcccaga gagcatgagg gttcacagct ctacctgcca ttcagacgac | 420 |
| gactgtattg ccggacagct ggacatgcaa ggcaatggga ttcgcacagg cactgtgta | 480 |
| ccctattacc atggggactc caagacctgc gaggtgtcag cctggtgccc ggtggaggat | 540 |
| ggaacttctg acaaccattt tctgggtaaa atggccccaa atttcaccat cctcatcaag | 600 |
| aacagcatcc actaccccaa gttcaagttc tcaaagggca acattgcaag ccagaagagt | 660 |
| gactacctca gcattgcac atttgatcag gactctgacc catactgtcc catcttcagg | 720 |
| ctgggtttca ttgttgagaa ggcaggagag aacttcacag aactggcaca aagggcggt | 780 |
| gtcattggag tcatcatcaa ctggaactgt gacctggact tgtctgaatc agagtgcaac | 840 |
| cccaaatatt cttttccggag gctcgacccc aagtatgacc ctgcctcctc aggctacaac | 900 |
| ttcaggtttg ccaagtatta caagataaac ggcactacca ccactcgaac tctcatcaaa | 960 |
| gcctatggga ttcgaatcga tgttatcgtg catggacagg cagggaaatt cagtctcatt | 1020 |
| cccaccatca tcaatctggc cactgctctg acctccatcg gggtgggctc cttcctgtgt | 1080 |
| gactggattt tgttaacgtt catgaacaaa aacaagctct acagccataa gaagttcgac | 1140 |
| aaggtgcgta ctccaaagca tccctcaagt agatggcctg tgaccttgc ccttgtcttg | 1200 |
| ggccagatcc ctcccccacc tagtcactac tcccaggatc agccacccag ccctccatca | 1260 |
| ggtgaaggac caactttggg agaagggca gagctaccac tggctgtcca gtctcctcgg | 1320 |
| ccttgctcca tctctgctct gactgagcag gtggtggaca cacttggcca gcatatggga | 1380 |
| caaagacctc ctgtccctga gccttcccaa caggactcca catccacgga ccccaaaggt | 1440 |
| ttggcccaac tttgatctca tcctcactaa actacagacc tggacctggg aaggcagaga | 1500 |
| cagctttggc tgctaaggca gtcctagaga agatctgcgc tcttcagtaa ccatgtccat | 1560 |
| gtgactggga aacagaaacc tgtgcaagag gacaggcgtc ttgctttagc ccaagcttac | 1620 |
| attcttcctc tccctaaggc ctctggggag aagtgggttc cctgccatct cctttcccaa | 1680 |
| cagaactcct cataggacct ttccctgctc acctcttgta ctctcataca gtattcaggg | 1740 |
| accccaagtt aggggctatg ctcctgttgt ataatttcaa gccccccttt agaagttgca | 1800 |
| gcatgctgag ttcaataaac cagtgatgag c | 1831 |

<210> SEQ ID NO 4
<211> LENGTH: 73
<212> TYPE: DNA
<213> ORGANISM: artificial
<220> FEATURE:
<223> OTHER INFORMATION: double stranded cloning cassette for lentivirus
      vectors for transgenesis and transient ion channel expression

<400> SEQUENCE: 4
ggatcccgta cgataacttc gtatagcata cattatacga agttatcgta cgggcgcgcc    60
cggaccggaa ttc                                                      73

<210> SEQ ID NO 5
<211> LENGTH: 76
<212> TYPE: DNA
<213> ORGANISM: artificial
<220> FEATURE:
<223> OTHER INFORMATION: 5' loxP cloning cassette

<400> SEQUENCE: 5
aagcttcgta cgataacttc gtatagcata cattatacga agttatagaa acagggatcc    60
tctagagcca ccatgg                                                   76

<210> SEQ ID NO 6
<211> LENGTH: 65
<212> TYPE: DNA
<213> ORGANISM: artificial
<220> FEATURE:
<223> OTHER INFORMATION: 3' loxP cloning cassette

<400> SEQUENCE: 6
gcggccgcta attagttgaa taacttcgta tagcatacat tatacgaagt tatcgtacgg    60
aattc                                                               65

<210> SEQ ID NO 7
<211> LENGTH: 283
<212> TYPE: DNA
<213> ORGANISM: artificial
<220> FEATURE:
<223> OTHER INFORMATION: probe for rat TRPV1

<400> SEQUENCE: 7
atggagcaac gggctagctt agactcagag gagtctgagt ccccaccccca agagaactcc   60 tgcctggacc ctccagacag agaccctaac tgcaagccac ctccagtcaa gccccacatc  120
ttcactacca ggagtcgtac ccggcttttt gggaagggtg actcggagga ggcctctccc  180
ctggactgcc cttatgagga aggcgggctg gcttcctgcc ctatcatcac tgtcagctct  240
gttctaacta ccagaggcc tggggatgga cctgccagtg tca                    283

<210> SEQ ID NO 8
<211> LENGTH: 195
<212> TYPE: DNA
<213> ORGANISM: artificial
<220> FEATURE:
<223> OTHER INFORMATION: probe for rat P2X2

<400> SEQUENCE: 8
ggtgaaggac caactttggg agaaggggca gagctaccac tggctgtcca gtctcctcgg    60
ccttgctcca tctctgctct gactgagcag gtggtggaca cacttggcca gcatatggga  120

```
caaagacctc ctgtccctga gccttcccaa caggactcca catccacgga ccccaaaggt        180
ttggcccaac tttga                                                         195
```